United States Patent
Wei et al.

(10) Patent No.: US 10,174,020 B2
(45) Date of Patent: Jan. 8, 2019

(54) PYRIDONE OR PYRIMIDONE DERIVATIVE, PREPARATION METHOD THEREFOR AND APPLICATION THEREOF

(71) Applicant: Sichuan Haisco Pharmaceutical Co., Ltd., Sichuan Province (CN)

(72) Inventors: Yonggang Wei, Sichuan Province (CN); Guanpeng Qiu, Sichuan Province (CN); Suxin Zheng, Sichuan Province (CN); Bolin Lei, Sichuan Province (CN); Yan Yu, Sichuan Province (CN); Yashu Chen, Sichuan Province (CN)

(73) Assignee: SICHUAN HAISCO PHARMACEUTICAL CO., LTD., Chengdu, Sichuan Providence (CN)

( * ) Notice: Subject to any disclaimer, the term of this patent is extended or adjusted under 35 U.S.C. 154(b) by 0 days.

(21) Appl. No.: 15/293,815

(22) Filed: Oct. 14, 2016

(65) Prior Publication Data

US 2017/0029423 A1    Feb. 2, 2017

Related U.S. Application Data

(63) Continuation of application No. PCT/CN2015/072236, filed on Feb. 4, 2015.

(30) Foreign Application Priority Data

Feb. 14, 2014  (CN) .......................... 2014 1 0052381

(51) Int. Cl.
| | |
|---|---|
| *C07D 487/04* | (2006.01) |
| *C07D 401/04* | (2006.01) |
| *C07D 401/10* | (2006.01) |
| *C07D 401/14* | (2006.01) |
| *C07D 471/04* | (2006.01) |

(52) U.S. Cl.
CPC ......... *C07D 471/04* (2013.01); *C07D 401/04* (2013.01); *C07D 401/10* (2013.01); *C07D 401/14* (2013.01); *C07D 487/04* (2013.01)

(58) Field of Classification Search
CPC .. C07D 401/04; C07D 401/10; C07D 401/14; C07D 471/04; C07D 487/04
See application file for complete search history.

(56) References Cited

U.S. PATENT DOCUMENTS

2005/0004149 A1   1/2005  Harada et al.

FOREIGN PATENT DOCUMENTS

| CN | 1222909 A | 7/1999 | | |
|---|---|---|---|---|
| CN | 1575290 A | 2/2005 | | |
| EP | 2978425 A2 | 2/2016 | | |
| EP | 2978756 A1 | 2/2016 | | |
| WO | 2008079787 A2 | 7/2008 | | |
| WO | 2013093484 A1 | 6/2013 | | |
| WO | WO 2014/154794 | * | 10/2014 | .......... C07D 413/14 |
| WO | WO 2014160592 | * | 10/2014 | .......... A61K 31/551 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*
International Search Report for PCT application No. PCT/CN2015/072236 dated Apr. 29, 2015.
Chinese Search Report for Chinese application No. 201580003159.1 dated May 19, 2017.
Chinese Office Action for Chinese application No. 201580003159.1 dated May 19, 2017.
European Search Report dated Nov. 30, 2017 for European application No. 15748809.9.

* cited by examiner

*Primary Examiner* — Erich A Leeser

(74) *Attorney, Agent, or Firm* — Ohlandt, Greeley, Ruggiero & Perle, LLP

(57) ABSTRACT

Provided is a pyridone or pyrimidone derivative(s) represented by general formula (I) and its preparation method and use. Substituents of the compound of general formula (I) are defined the same as in the specification.

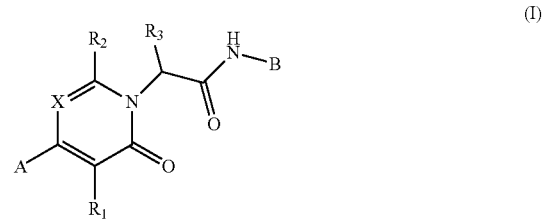

8 Claims, No Drawings

PYRIDONE OR PYRIMIDONE DERIVATIVE, PREPARATION METHOD THEREFOR AND APPLICATION THEREOF

TECHNICAL FIELD

The present invention relates topyridone or pyrimidone derivative(s) represented by general formula (I) or a stereoisomer, an oxynitride, a hydrate, a solvate, a metabolite, a pharmaceutically acceptable salt or prodrug thereof, a preparation method therefor, a pharmaceutical composition containing the same, and use thereof as an inhibitor of blood-coagulation factor XIa.

BACKGROUND ART

Blood coagulation is the result of coordinated activation of various plasma proteases, their co-factors, and platelets. This cascade reaction is divided into the intrinsic (contact activation) pathway, the extrinsic (tissue factor activation) pathway, and the common pathway (prothrombin and thrombin generation) pathway (Gailani and Renne, 2007, Arterioscler Thromb Vasc Biol, 27, 2507-2513; Gailani and Renne, 2007, J Thromb Haemost, 5, 1106-1112; Mackman, Tilley et al., 2007, Arterioscler Thromb Vasc Biol, 27, 1687-1693). In the blood coagulation process, the most important physiological activator is tissue factor. Under physiological conditions, tissue factor is expressed on the vessel wall, while under pathological conditions tissue factor is expressed in circulating monocytes and microparticles. The tissue factor-factor VIIa complex catalyzes the formation of factor Xa, and factor Xa in turn cleaves prothrombin to produce thrombin. In the intrinsic blood-coagulation pathway, factor XIa is catalytically produced by contact with activator XIIa, which in turn leads to the activation of factor IX and factor X. Factor XIa is only involved in the intrinsic pathway. In the absence of an injury, abnormal thrombosis at the base of the vessel wall is achieved by the intrinsic pathway. In addition, thrombin and the tissue factor-factor VIIa complex can also activate intrinsic coagulation proteases, resulting in pathways closely related to blood-coagulation. Blood-coagulation and activation of platelets lead to thrombosis and hemostasis, and are regulated by local plasmin (Schumacher, Luettgen et al., 2010, Arterioscler Thromb Vasc Biol, 30, 388-392).

Hemostasis is an advantageous process for the maintenance of the liquid state of blood and protection of the integrity of blood vessels. Thrombosis is a disadvantageous process that causes blood vessel occlusion, and is the major cause of cardiovascular morbidity and mortality. Currently there are many drugs for treatment of thromboembolism, including anticoagulants (such as heparin and warfarin), fibrinolytic agents (such as streptokinase and urokinase), and platelet inhibitors (such as aspirin) as commonly used in clinical settings. However, these antithrombotic drugs for treatment of cardiovascular diseases have the drug-related side effect—bleeding. For example, heparin as an antithrombotic agent has a highly variable dose-dependent response, and its anticoagulation action must be closely monitored to avoid the risk of severe bleeding. The platelet inhibitor aspirin given at high doses will cause the risk of gastrointestinal bleeding. This necessitates selecting a molecular target to distinguish between hemostasis and thrombosis, such that the thrombin is reduced to a level enough to prevent thrombosis while the hemostatic function of the mechanism can be maintained with a sufficient level of thrombin remained (Schumacher, Luettgen et al., 2010, Arterioscler Thromb Vasc Biol, 30, 388-392).

Factor XIa can improve the production of blood clots and their stability in vitro. Factor XIa can increase production of thrombin during coagulation that is activated by a low level of tissue factor or thrombin. During coagulation activated by a higher level of tissue factor, the prothrombin time (TP) is not affected by the inhibition of factor XIa, whereas the activated partial thromboplastin time (aPTT) in the contact activation pathway is affected by the inhibition of factor XIa. Thus, inhibition of factor XIa can limit the amplification by thrombin resulting from the intrinsic cascade reaction, but has only a limited effect on the coagulation cascadereaction activated by tissue factor (von dem Borne, Cox et al., 2006, Blood Coagul Fibrinolysis, 17, 251-257).

In addition to affecting the production of thrombin, factor XI also plays a role in anti-fibrinolysis. The factor XI-dependent amplification by thrombin also leads to activation of the thrombin-activated plasmin inhibitor, and this inhibitor renders blood clots resistant to plasmin. That is, inhibition of factor XI may directly increase lysis of blood clots (Bouma, Marx et al., 2001, Thromb Res, 101, 329-354).

The potential of factor XI as a safe therapeutic target is convincingly demonstrated in hemophilia C patients. Factor XI-deficient hemophilia C patients have only a minor bleeding phenotype as compared to patients with hemophilia A (factor VIII deficiency) or hemophilia B (factor IX deficiency) (Gomez and Bolton-Maggs, 2008, Haemophilia, 14, 1183-1189; Duga and Salomon, 2009, Semin Thromb Hemost, 35, 416-425; Seligsohn, 2009, J Thromb Haemost, 7 Suppl 1, 84-87). Unlike hemophilia A or B, hemophilia C occurs in both genders. Patients with over 180 mutation types of haemophilia C have a low frequency of haemorrhage and rarely bleed spontaneously, and mild to moderate bleeding is more likely to occur in tissues particularly prone to fibrinolysis (such as the oral or urogenital system) generally after surgery or trauma. Although hemophilia C patients have an extended aPTT, the bleeding and coagulation levels are less related to each other. Severe factor XI deficiency can cause excessive bleeding in women during menstruation, but does not necessarily affect pregnancy and parturition of female patients. Bleeding associated with factor XI deficiency can be treated by the factor XI substitutive therapy with recombinant coagulation factors. Severe factor XI deficiency is usually a genetically inherited coagulation disorder, thus patients of this type are rare, and the phenotype is variable. In contrast, blood-coagulation factor V deficiency shows poor tolerability (Asselta and Peyvandi, 2009, Semin Thromb Hemost, 35, 382-389), and blood-coagulation factor X deficiency shows very serious phenotypes (Menegatti and Peyvandi, 2009, Semin Thromb Hemost, 35, 407-415).

Many findings on human and laboratory animals indicate that targeting factor XI/factor XIa may reduce the risk of certain thromboembolic diseases, and shows a much lower bleeding frequency as compared to the factors in the blood coagulation pathway that are currently targeted for an antithrombotic purpose (such as factor Xa, thrombin, etc.), despite the potential side effect of bleeding. Therefore, inhibiting factor XI may be now one of effective approaches to antithrombotic treatment of patients who may bleed.

Currently there are a limited number of candidate agents targeting factor XI, including factor XI antibodies, factor XI antisense nucleotides (ASOs), proteins or polypeptides, small chemical molecules, and a natural product isolated from sponges. Although factor XI ASOs are advantageous in that the deficiency of factor XIa caused by the ASOs therapy may be easily reversed by supplementing concentrated plasma-derived factor XIa (Zhang, Lowenberg et al., 2010, Blood, 116, 4684-4692), they take effect relatively slowly, and their antithrombotic effect is relatively weak. Small-molecule organic compounds have many advantages, such as good bioavailability upon oral administration and better patient compliance.

WO2013056034 describes novel substituted tetrahydroisoquinolines and derivatives thereof, as a blood-coagulation factor FXIa or plasma kallikrein inhibitor, is useful for treatment and prevention of thromboembolic diseases and has the following structural formula:

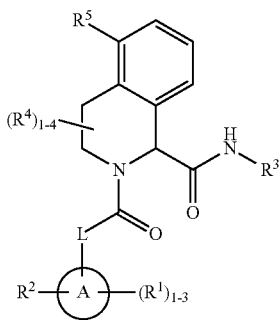

where A is a carbocycle; L is a linking group, such as a direct bond, alkyl, alkenyl, or alkynyl; and $R^1$ to $R^5$ are halogen, alkyl, alkoxy, and the like. It is not to be construed that the specific disclosure in this patent document is a part of the present invention.

WO2013055984 describes novel substituted tetrahydroisoquinolines and derivatives thereof, as a blood-coagulation factor FXIa or plasma kallikrein inhibitor, is useful for treatment and prevention of thromboembolic diseases and has the following structural formula:

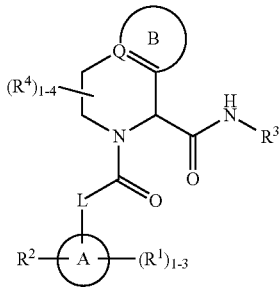

where A is a carbocycle, B is a heterocycle, Q is C or N, L is a linking group such as a direct bond, alkyl, alkenyl or alkynyl, and $R^1$ to $R^5$ are halogen, alkyl, alkoxy, and the like. It is not to be construed that the specific disclosure in this patent document is a part of the present invention.

WO2013056060 describes novel substituted heterocyclic derivatives, as a blood-coagulation factor FXIa or plasma kallikrein inhibitor, is useful for treatment and prevention of thromboembolic diseases and has the following structural formula:

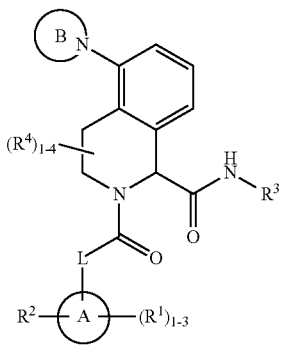

where A is a carbocycle, B is a heterocycle, L is a linking group such as a direct bond, alkyl, alkenyl or alkynyl, and $R^1$ to $R^5$ are halogen, alkyl, alkoxy, and the like. It is not to be construed that the specific disclosure in this patent document is a part of the present invention.

WO2013093484 describes pyrimidone or pyridone derivatives as a blood-coagulation factor FXIa inhibitor having the following structural formula, and use thereof for treatment and prevention of thromboembolic diseases:

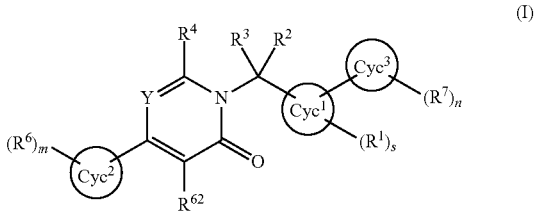

(I)

where $Cyc^1$, $Cyc^2$ and $Cyc^3$ are each a carbocycle or a heterocycle, and the substituents may be halogen, alkyl, alkoxy, and the like. It is not to be construed that the specific disclosure in this patent document is a part of the present invention.

WO2013118805 describes pyrrolidine derivatives as a blood-coagulation factor FXIa inhibitor having the following structural formula, and use thereof for treatment and prevention of thromboembolism and associated diseases:

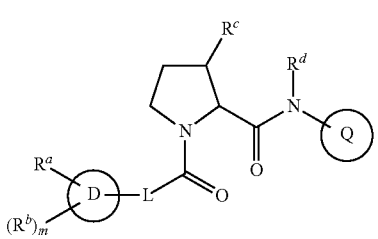

(1)

where D and Q are each a carbocycle or a heterocycle, and the substituents may be halogen, alkyl, alkoxy, carbocycle, heterocycle and the like. It is not to be construed that the specific disclosure in this patent document is a part of the present invention.

The present invention aims to provide a novel bioactive compound as an inhibitor of blood-coagulation factor FXIa, which is useful for treatment of various diseases and complications caused by thrombosis, such as venous thrombosis, deep vein thrombosis, deep vein thrombosis of lower extremity, thrombophlebitis, cerebral arterial thrombosis, arterial embolism, coronary thrombosis, pulmonary embolism, cerebral embolism, renal embolism, hepatic vein thrombosis, portal vein thrombosis, chronic disseminated intravascular coagulation, limb and central microvascular arterial embolism, atherosclerosis, acute coronary syndrome, unstable angina, acute coronary arterial syndrome, myocardial infarction, arteriosclerosis, sudden ischemic death, transient ischemia, peripheral arterial occlusive disease, stroke, non-bacterial thrombotic endocarditis with arterial embolism, cerebrovascular disease and the like.

SUMMARY OF INVENTION

The present invention relates to a compound represented by general formula (I) which is selected from the compounds represented by general formula (II), or a stereoisomer, an oxynitride, a hydrate, a solvate, a metabolite, a pharmaceutically acceptable salt, co-crystal or prodrug thereof:

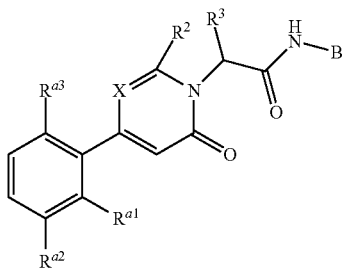

(II)

wherein $R^2$ is selected from H, F, Cl, Br, I or a $C_{1-4}$ alkyl, preferably H, F, Cl or Br;

$R^3$ is selected from hydrogen, a $C_{1-4}$ alkyl or —$(CH_2)_n$-(5- or 6-membered carbocycle), preferably H, methyl, ethyl or benzyl, wherein the carbocycle is optionally further substituted with 0 to 5 (preferably 1 to 5) substituents selected from H, F, Cl, Br, I, hydroxy, amino, carboxy, a $C_{1-4}$alkyl or a $C_{1-4}$alkoxy;

alternatively, $R^2$ and $R^3$ may form, together with the atoms attached thereto, a 5- to 6-membered heterocycle, preferably a 5-membered heterocycle, containing 1 to 4 heteroatoms selected from N, O or S, wherein the heterocycle is optionally further substituted with 0 to 3 (preferably 1 to 3) substituents selected from H, F, Cl, Br, I, hydroxy, a $C_{1-4}$alkyl or a $C_{1-4}$alkoxy;

$R^{a1}$, $R^{a2}$ or $R^{a3}$ is each independently selected from H, F, Cl, Br, I, cyano, formyl, acetyl, a $C_{1-4}$ alkyl, a $C_{1-4}$ alkoxy, —C(=O)$C_{1-4}$alkyl or a 5-membered heterocycle, preferably H, F, Cl, Br, cyano, formyl, acetyl, methyl, methoxy or tetrazolyl, wherein the heterocycle contains 1 to 4 heteroatoms selected from N, O or S, and the alkyl, alkoxy or heterocycle is optionally further substituted with 0 to 5 (preferably 1 to 5) substituents selected from H, F, Cl, Br or I;

B is selected from one of the following structures, which is substituted or unsubstituted:

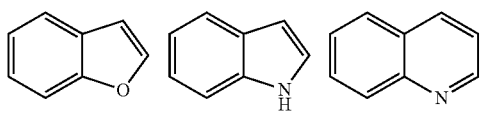

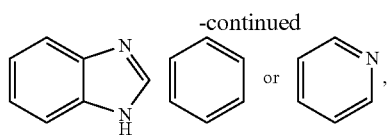

-continued preferably

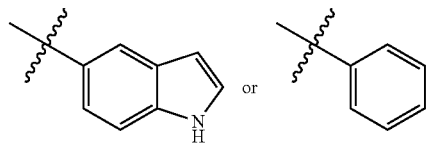 [SMILES: *c1ccc2[nH]ccc2c1 ; *c1ccccc1]

which is substituted or unsubstituted; and if substituted, it is optionally substituted with 1 to 5 $R^b$s, wherein the $R^b$s are each independently selected from H, F, Cl, Br, I, hydroxyl, amino, carboxy, —NHC(=O)$R^{b2}$, —C(=O)N$R^{b1}R^{b2}$ or —C(=O)$R^{b1}$; $R^{b1}$ and $R^{b2}$ are each independently selected from H, hydroxy, amino, a $C_{1-4}$alkyl or a $C_{1-4}$alkoxy, preferably H, hydroxy, amino, trifluoromethyl, methyl, ethyl, isopropyl, methoxy or ethoxy, wherein the alkyl or alkoxy is optionally further substituted with 0 to 4 (preferably 1 to 4) substituents selected from H, F, Cl, Br, I or hydroxyl;

X is selected from N or CH; and n is selected from 0, 1, 2, 3, or 4.

In a preferred embodiment of the present invention, provided is a compound represented by general formula (II) which is selected from the compounds represented by general formula (III), or a stereoisomer, an oxynitride, a hydrate, a solvate, a metabolite, a pharmaceutically acceptable salt, co-crystal or prodrug thereof:

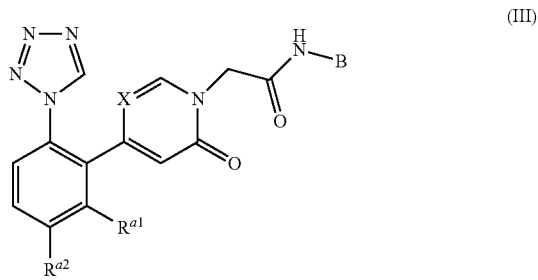

(III)

wherein $R^{a1}$ or $R^{a2}$ is each independently selected from H, F, Cl, Br, I, cyano, formyl, acetyl, a $C_{1-4}$ alkyl, or a $C_{1-4}$ alkoxy, preferably H, F, Cl, or Br, wherein the alkyl or alkoxy is optionally further substituted with 0 to 5 (preferably 1 to 5) substituents selected from H, F, Cl, Br or I;

B is selected from one of

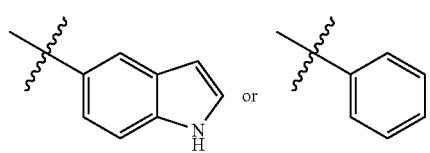 [SMILES: *c1ccc2[nH]ccc2c1 ; *c1ccccc1]

which is substituted or unsubstituted; and if substituted, it is optionally substituted with 1 to 5 $R^b$s, wherein the $R^b$s are each independently selected from H, F, Cl, Br, I, hydroxyl, amino, carboxy, —NHC(=O)R$^{b2}$, —C(=O)NR$^{b1}$R$^{b2}$ or —C(=O)R$^{b1}$, preferably H, carboxy, —C(=O)NH$_2$ or —NHC(=O)OCH$_3$; R$^{b1}$ and R$^{b2}$ are each independently selected from H, hydroxy, amino, trifluoromethyl, methyl, ethyl, isopropyl, methoxy or ethoxy.

In a preferred embodiment of the present invention, provided is a compound represented by general formula (II) which is selected from the compounds represented by general formula (IV), or a stereoisomer, an oxynitride, a hydrate, a solvate, a metabolite, a pharmaceutically acceptable salt, co-crystal or prodrug thereof:

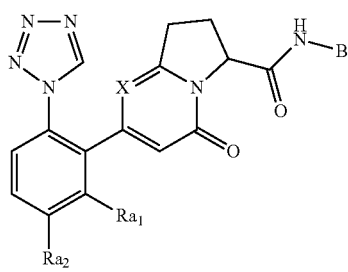
(IV)

wherein R$^{a1}$ or R$^{a2}$ is each independently selected from H, F, Cl, Br, I, cyano, formyl, acetyl, a C$_{1-4}$ alkyl, or a C$_{1-4}$ alkoxy, preferably H, F, Cl, or Br, wherein the alkyl or alkoxy is optionally further substituted with 0 to 5 (preferably 1 to 5) substituents selected from H, F, Cl, Br or I;

B is selected from one of

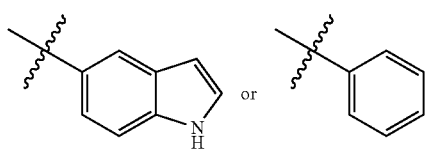 [SMILES: *c1ccc2[nH]ccc2c1 ; *c1ccccc1]

which is substituted or unsubstituted; and if substituted, it is optionally substituted with 1 to 5 R$^b$s, wherein the R$^b$s are each independently selected from H, F, Cl, Br, I, hydroxyl, amino, carboxy, —NHC(=O)R$^{b2}$, —C(=O)NR$^{b1}$R$^{b2}$ or —C(=O)R$^{b1}$, preferably H, carboxy, —C(=O)NH$_2$ or —NHC(=O)OCH$_3$; R$^{b1}$ and R$^{b2}$ are each independently selected from H, hydroxy, amino, trifluoromethyl, methyl, ethyl, isopropyl, methoxy or ethoxy.

In a preferred embodiment of the present invention, provided is a compound selected from:

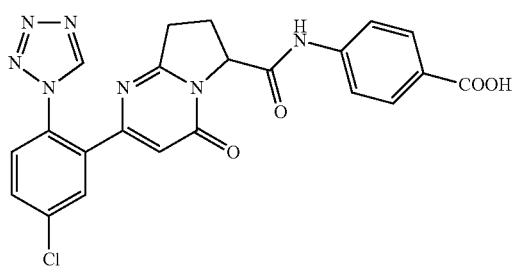

-continued

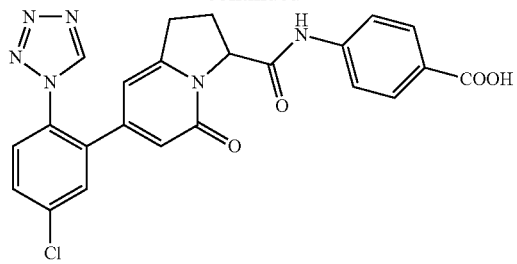

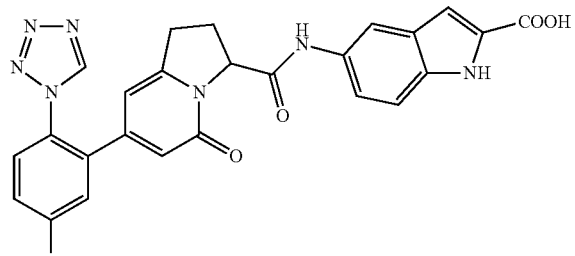

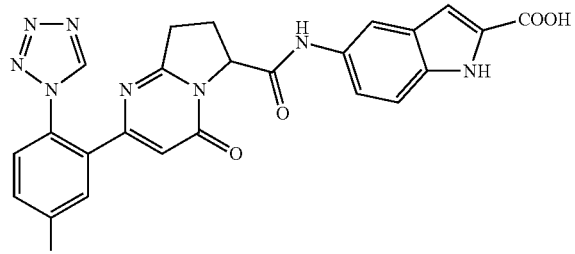

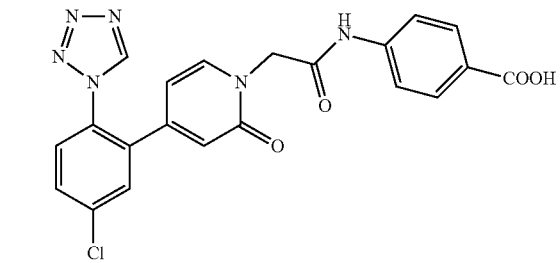

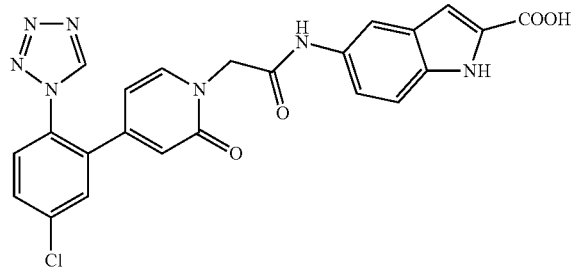

-continued

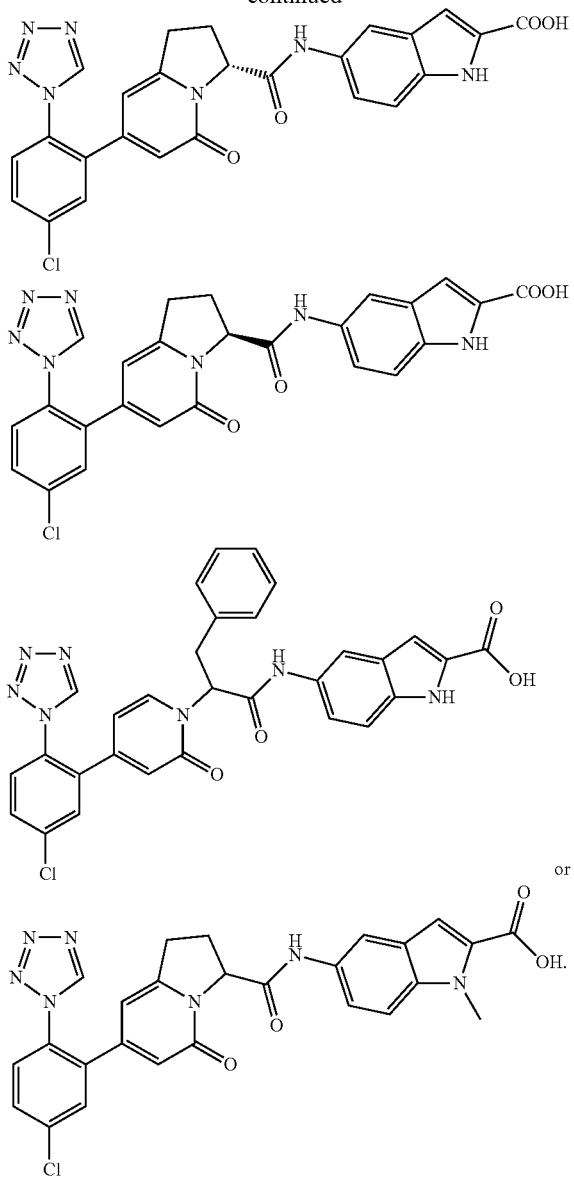

or

The present invention relates to use of the compound as above described, or a stereoisomer, an oxynitride, a hydrate, a solvate, a metabolite, a pharmaceutically acceptable salt, co-crystal or prodrug thereof, in the manufacture of a medicament for treatment of diseases associated with blood-coagulation factor XIa, wherein the diseases associated with blood-coagulation factor XIa are selected from thromboembolic diseases, including venous thrombosis, deep vein thrombosis, thrombophlebitis, cerebral arterial thrombosis, arterial embolism, coronary thrombosis, pulmonary embolism, renal embolism, cerebral embolism, atherosclerosis, acute coronary syndrome, unstable angina, acute coronary arterial syndrome, myocardial infarction, arteriosclerosis, sudden ischemic death, transient ischemia, peripheral arterial occlusive disease, stroke, or cerebrovascular diseases.

The present invention provides a method for treating diseases associated with blood-coagulation factor XIa, wherein the diseases associated with blood-coagulation factor XIa are selected from thromboembolic diseases, including venous thrombosis, deep vein thrombosis, thrombophlebitis, cerebral arterial thrombosis, arterial embolism, coronary thrombosis, pulmonary embolism, renal embolism, cerebral embolism, atherosclerosis, acute coronary syndrome, unstable angina, acute coronary arterial syndrome, myocardial infarction, arteriosclerosis, sudden ischemic death, transient ischemia, peripheral arterial occlusive disease, stroke, or cerebrovascular diseases.

Unless otherwise indicated, the terms used throughout the specification and claims have the following meanings.

When referring to substitution with more substituents, the substituents may be the same as or different from each other.

When referring to inclusion of more heteroatoms, the heteroatoms may be the same as or different from each other.

All of the carbon, hydrogen, oxygen, sulfur, nitrogen or halogen involved in the groups and compounds according to the present invention include their isotopes. All of the carbon, hydrogen, oxygen, sulfur, nitrogen or halogen involved in the groups and compounds according to the present invention are optionally further replaced by one or more of their corresponding isotopes, wherein the carbon isotopes include $^{12}C$, $^{13}C$ and $^{14}C$, the hydrogen isotopes include protium (H), deuterium (D, also known as heavy hydrogen) and tritium (T, also known as superheavy hydrogen), the oxygen isotopes include $^{16}O$, $^{17}O$ and $^{18}O$, the sulfur isotopes include $^{32}S$, $^{33}S$, $^{34}S$ and $^{36}S$, the nitrogen isotopes include $^{14}N$ and $^{15}N$, the fluorine isotopes include $^{19}F$, the chlorine isotopes include $^{35}Cl$ and $^{37}Cl$, and the bromine isotopes include $^{79}Br$ and $^{81}Br$.

A "pharmaceutically acceptable salt" refers to a salt of a pharmaceutically acceptable non-toxic acid or base, including salts of inorganic or organic acid and bases.

A "co-crystal" refers to a crystal formed by an active pharmaceutical ingredient (API) and a cocrystal former (CCF) combined by hydrogen bonds or other non-covalent bonds, wherein both API and CCF when in their pure form are solid at room temperature and these components are present in a fixed stoichiometric ratio therebetween. A co-crystal is a multi-component crystal, including both a binary co-crystal formed by two neutral solids and a multiple co-crystal formed by a neutral solid and a salt or solvate.

A "stereoisomer" refers to an isomer of a molecule having its atoms in a different spatial arrangement, including cis-trans-isomer, enantiomer, and conformer.

A "prodrug" means a compound that can be converted under physiological conditions or under the action of solvent into the biologically active compound of the present invention. A prodrug of the present invention is prepared by modification of a functional group in the compound of the present invention. Such a modification can be removed in vivo or by conventional operations, so as to produce the parent compound. A prodrug includes compounds formed by attaching any group to a hydroxyl, amino or mercapto group in the compound of the present invention. When a prodrug of the compound of the present invention is administered to a mammalian individual, it is cleaved to give free hydroxyl, free amino or free mercapto groups. Examples of a prodrug include, but are not limited to, compounds formed by reaction of the hydroxyl or amino functional groups in the compound of the present invention with formic acid, acetic acid or benzoic acid.

DETAILED DESCRIPTION OF INVENTION

Hereinafter the technical solutions of the present invention will be described in details in conjunction with the drawings and examples. However, the scope of the present invention includes but is not limited to these.

The structures of compounds were determined by nuclear magnetic resonance (NMR) and/or mass spectroscopy (MS). NMR shifts (δ) are presented in $10^{-6}$ ppm. NMR measurements were performed with an NMR device (Bruker ADVANCE III 400 and Bruker ADVANCE 300), wherein the measurement solvents were hexadeuterodimethyl sulfoxide (DMSO-d6), deuterochloroform ($CDCl_3$), and deuteratedmethanol ($CD_3OD$), and the internal reference was tetramethylsilane (TMS).

MS measurements were performed with Agilent 6120B (ESI) and Agilent 6120B (APCI).

HPLC measurements were performed with Agilent 1260 DAD High-pressure Liquid Chromatograph (Zorba x SB-C18 100×4.6 mm).

Thin-layer chromatography silica gel plate used was: HSGF254 silica gel plate (Huanghai, Yantai) or GF254 silica gel plate (Qingdao). The specification of the silica gel plate used for thin-layer chromatography (TLC) was 0.15 mm to 0.20 mm, while the specification of isolated and purified product by TLC was 0.4 mm to 0.5 mm.

The chromatography column generally used the silica gel (Huanghai, Yantai) of 200 to 300 mesh as a carrier.

Known starting materials used in connection with the present invention can be synthesized following or using methods known in the art, or can be purchased from companies such as Titansci, Energy Chemical, Demochem (Shanghai), Kelong Chemical (Chengdu), Accela ChemBio, and J&K Scientific.

A nitrogen atmosphere means that the reaction vessel is connected to a $N_2$ balloon of about 1 L in volume.

A hydrogen atmosphere means that the reaction vessel is connected to a $H_2$ balloon of about 1 L in volume.

Hydrogenation reactions generally involve a vacuuming and $H_2$-charging operation, repeating 3 times.

In the Example, unless particularly specified, reactions were carried out under a $N_2$ atmosphere.

In the Example, unless particularly specified, solutions refer to aqueous solutions.

In the Example, unless particularly specified, reaction temperatures are room temperature.

The room temperature as the most suitable reaction temperature is 20° C. to 30° C.

Et: ethyl;
Me: methyl;
Bn: benzyl;
Bz: benzyol.

Intermediate 1

2-(5-chloro-2-(1H-tetrazol-1-yl)phenyl)-4-oxo-4,6,7,8-tetrahydropyrrolo[1,2-a]pyrimidine-6-carboxylic Acid (Intermediate 1)

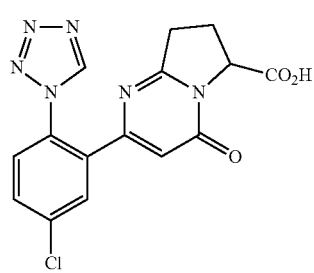

Intermediate 1

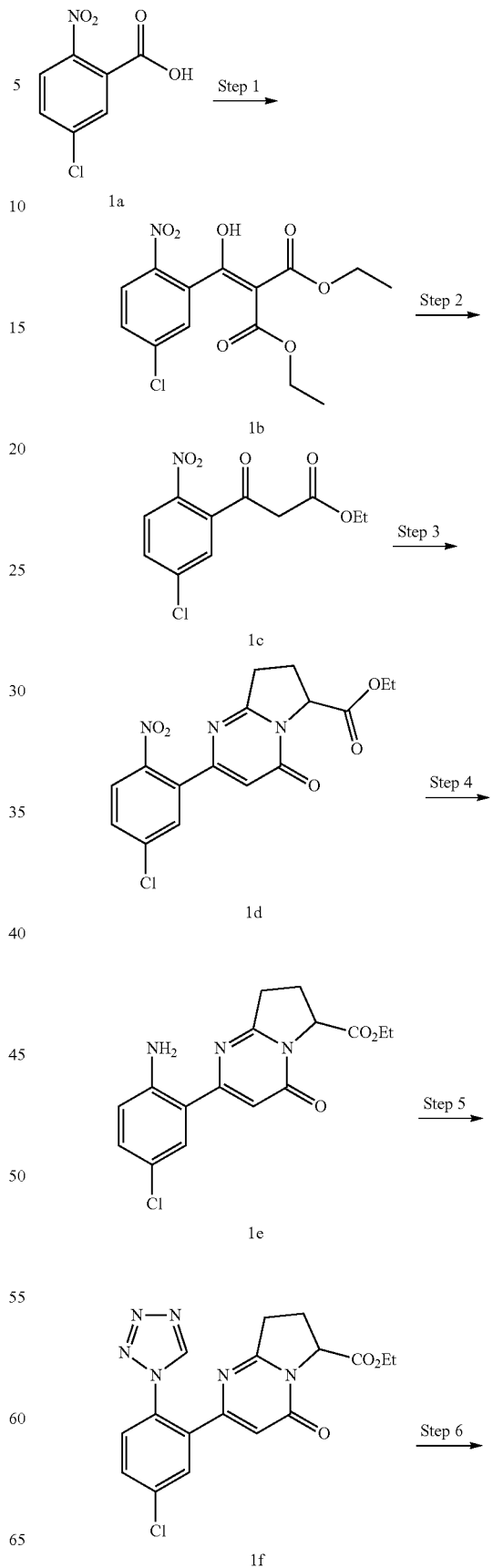

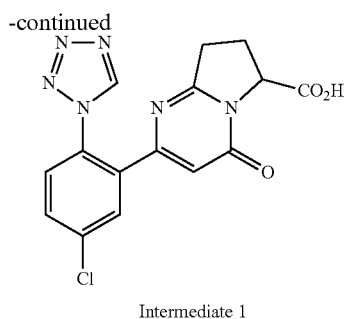

Intermediate 1

Step 1: diethyl 2-((5-chloro-2-nitrophenyl)(hydroxy)methylene)malonate (1b)

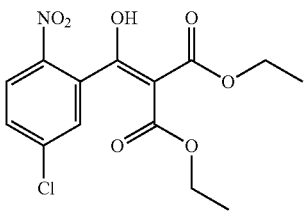 [SMILES: CCOC(=O)C(C(=O)OCC)=C(O)c1cc(Cl)ccc1[N+](=O)[O-]]

5-chloro-2-nitrobenzoic acid (1a) (10.12 g, 50.2 mmol) and dichlorosulfoxide (7.17 g, 60.3 mmol) were dissolved in an anhydrous toluene (40 mL), urea (0.30 g, 5 mmol) was added thereto, the temperature was raised to 100° C. to allow the reaction to proceed for 3 hours, and then cooled to room temperature, to obtain reaction liquid 1; diethyl malonate (8.05 g, 50.2 mmol), magnesium (1.30 g, 53.4 mmol), ethanol (7.6 g, 165 mmol) and tetrachloromethane (21 mL) were added to toluene (80 mL), the reaction was allowed to proceed for 1 hour at room temperature, the temperature was raised to reflux for 1 hour, and cooled to 5° C., to obtain reaction liquid 2; reaction liquid 1 was added to reaction solution 2 and allowed to react at room temperature for 1 hour; a hydrochloric acid solution (wt=10%, 20 ml) was added to the reaction solution to partition the mixed solution; the aqueous phase was extracted with ethyl acetate (50 mL×3); the organic phases were combined, washed with water (50 mL×2), dried over anhydrous sodium sulfate, and concentrated; the residue was purified by silica gel column chromatography (petroleum ether:ethyl acetate=0:1 to 3:1) to give the title compound diethyl 2-((5-chloro-2-nitrophenyl)(hydroxy)methylene)malonate (1b) as a colorless liquid (5.0 g, yield 29%).

$^1$H NMR (400 MHz, CDCl$_3$) δ 14.21 (s, 1H), 8.14 (d, 1H), 7.58 (m, 1H), 7.40 (d, 1H), 4.22 (m, 4H), 1.27 (dt, 6H).

Step 2: ethyl 3-(5-chloro-2-nitrophenyl)-3-oxopropanoate (1c)

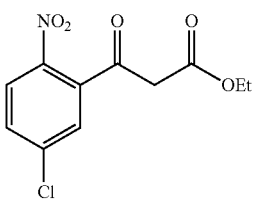 [SMILES: CCOC(=O)CC(=O)c1cc(Cl)ccc1[N+](=O)[O-]]

Diethyl 2-((5-chloro-2-nitrophenyl)(hydroxy)methylene)malonate (1b) (4.0 g, 11.6 mmol) was dissolved in water (40 mL), p-toluenesulfonic acid (0.11 g, 0.66 mmol) was added thereto, and the temperature was raised to reflux for 6 hours. The reaction solution was cooled to room temperature and extracted with ethyl acetate (50 ml×2); the organic phases were combined, dried over anhydrous sodium sulfate, and concentrated; the residue was purified by silica gel column chromatography (petroleum ether:ethyl acetate=50:1 to 3:1) to give the title compound ethyl 3-(5-chloro-2-nitrophenyl)-3-oxopropanoate (1c) as a light brown solid (2.5 g, yield 79%).

$^1$H NMR (400 MHz, CDCl$_3$) δ 8.13 (d, 1H), 7.59 (dd, 1H), 7.49 (d, 1H), 4.17 (q, 2H), 3.86 (s, 2H), 1.25 (t, 3H).

Step 3: ethyl 2-(5-chloro-2-nitrophenyl)-4-oxo-4,6,7,8-tetrahydropyrrolo[1,2-a]pyrimidine-6-carboxylate (1d)

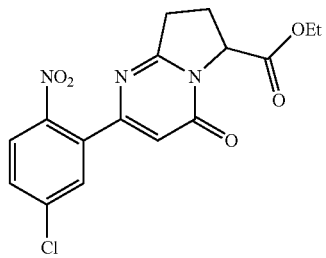 [SMILES: CCOC(=O)C1CCc2nc(-c3cc(Cl)ccc3[N+](=O)[O-])cc(=O)n21]

Ethyl 3-(5-chloro-2-nitrophenyl)-3-oxopropanoate (1c) (0.45 g, 1.65 mmol) was dissolved in o-xylene (5 mL), then ethyl 5-amino-2H-3,4-dihydropyrazole-2-carboxylate (0.27 g, 1.73 mmol) and 1,8-diazabicyclo[5.4.0]undec-7-ene (0.924 g, 6.07 mmol) were added thereto, and the temperature was raised to 130° C. at which the reaction was allowed to proceed for half an hour. The reaction solution was concentrated, and the residue was purified by silica gel column chromatography (petroleum ether:ethyl acetate=5:1 to 3:1) to give the title compound ethyl 2-(5-chloro-2-nitrophenyl)-4-oxo-4,6,7,8-tetrahydropyrrolo[1,2-a]pyrimidine-6-carboxylate (1d) as a light yellow solid (50 mg, yield 9%).

$^1$H NMR (400 MHz, DMSO) δ 8.05 (d, 1H), 7.88 (d, 1H), 7.81 (dd, 1H), 6.72 (s, 1H), 5.09 (dd, 1H), 4.19 (q, 2H), 3.08 (m, 2H), 2.59 (m, 1H), 2.18 (m, 1H), 1.23 (m, 3H).

Step 4: ethyl 2-(5-chloro-2-aminophenyl)-4-oxo-4,6,7,8-tetrahydropyrrolo[1,2-a]pyrimidine-6-carboxylate (1e)

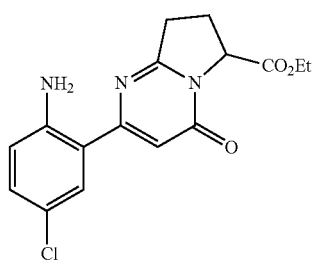 [SMILES: CCOC(=O)C1CCc2nc(-c3cc(Cl)ccc3N)cc(=O)n21]

Ethyl 2-(5-chloro-2-nitrophenyl)-4-oxo-4,6,7,8-tetrahydropyrrolo[1,2-a]pyrimidine-6-carboxylate (1d) (70 mg, 0.19 mmol) was dissolved in ethyl acetate (3 ml), and stannous chloride dihydrate (148 mg, 0.65 mmol) and hydrochloric acid (6M, 43.7 mg, 1.2 mmol) were added thereto, and the temperature was raised to reflux for 4 hours. The reaction solution was concentrated, and the residue was purified by silica gel column chromatography (petroleum ether:ethyl acetate:methanol=20:20:1) to give the title compound ethyl 2-(5-chloro-2-aminophenyl)-4-oxo-4,6,7,8-tetrahydropyrrolo[1,2-a]pyrimidine-6-carboxylate (1e) as a yellow solid (140 mg, yield 110%, the product contains some residual solvent).

$^1$H NMR (400 MHz, DMSO) δ 7.44 (d, 1H), 7.14 (dd, 1H), 6.76 (d, 1H), 6.54 (s, 1H), 6.29 (s, 2H), 5.04 (dd, 1H), 4.03 (q, 2H), 3.17 (m, 2H), 2.62 (m, 1H), 2.18 (m, 1H), 1.18 (m, 3H).

Step 5: ethyl 2-(5-chloro-2-(1H-tetrazol-1-yl)phenyl)-4-oxo-4,6,7,8-tetrahydropyrrolo[1,2-a]pyrimidine-6-carboxylate (1f)

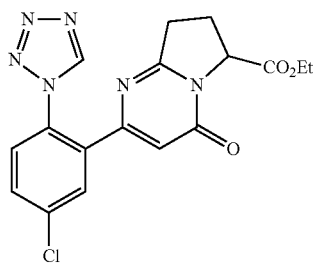 [SMILES: CCOC(=O)C1CCc2nc(-c3cc(Cl)ccc3-n3cnnn3)cc(=O)n21]

Ethyl 2-(5-chloro-2-aminophenyl)-4-oxo-4,6,7,8-tetrahydropyrrolo[1,2-a]pyrimidine-6-carboxylate (1e) (140 g, 0.42 mmol) was dissolved in acetic acid (3 mL), trimethyl orthoformate (223.3 mg, 2.1 mmol) was added thereto, and the reaction was allowed to proceed for 30 min. Sodium azide (115.5 g, 2.1 mmol) was added thereto, and the temperature was raised to 75° C. to allow the reaction to proceed for 3 hours. The reaction solution was concentrated, and water (10 ml) and dichloromethane (10 ml) were added thereto to partition the liquid. The aqueous phase was extracted with dichloromethane (10 ml×2); the organic phases were combined, dried over anhydrous sodium sulfate, and concentrated; the residue was purified by silica gel column chromatography (dichloromethane:methanol=99:1 to 98:2) to give the title compound ethyl 2-(5-chloro-2-(1H-tetrazol-1-yl)phenyl)-4-oxo-4,6,7,8-tetrahydropyrrolo[1,2-a]pyrimidine-6-carboxylate (1f) as a light yellow solid (140 mg, yield 86%).

$^1$H NMR (400 MHz, CDCl$_3$) δ 8.76 (s, 1H), 7.70 (d, 1H), 7.63 (dd, 1H), 7.50 (d, 1H), 6.42 (s, 1H), 5.03 (dd, 1H), 4.26 (m, 2H), 3.02 (m, 1H), 2.84 (m, 1H), 2.51 (m, 1H), 2.25 (m, 1H), 1.31 (t, 3H).

Step 6

2-(5-chloro-2-(1H-tetrazol-1-yl)phenyl)-4-oxo-4,6,7,8-tetrahydropyrrolo[1,2-a]pyrimidine-6-carboxylic Acid (Intermediate 1)

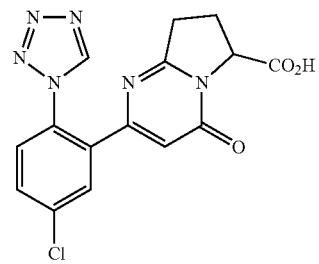 [SMILES: O=C(O)C1CCc2nc(-c3cc(Cl)ccc3-n3cnnn3)cc(=O)n21]

Ethyl 2-(5-chloro-2-(1H-tetrazol-1-yl)phenyl)-4-oxo-4,6,7,8-tetrahydropyrrolo[1,2-a]pyrimidine-6-carboxylate (1f) (140 mg, 0.36 mmol) was dissolved in tetrahydrofuran (3 mL), lithium hydroxide (30.2 mg, 0.72 mmol) was added thereto, and the reaction was allowed to proceed at room temperature for 3 hours. Potassium hydrogen sulfate was added to the reaction solution, and the solution was adjusted to pH=5 to 6 and extracted with ethyl acetate (20 ml×3); the organic phases were combined, dried over anhydrous sodium sulfate, and concentrated; the residue was purified by silica gel column chromatography (dichloromethane:methanol=9:1) to give the title compound 2-(5-chloro-2-(1H-tetrazol-1-yl)phenyl)-4-oxo-4,6,7,8-tetrahydropyrrolo[1,2-a]pyrimidine-6-carboxylic acid (Intermediate 1) as a light yellow solid (120 mg, yield 93%).

$^1$H NMR (400 MHz, CDCl$_3$) δ 8.83 (s, 1H), 7.72 (d, 1H), 7.64 (dd, 1H), 7.53 (dd, 1H), 6.47 (s, 1H), 5.10 (dd, 1H), 3.07 (m, 1H), 2.87 (m, 1H), 2.48 (m, 2H).

Intermediate 2

7-(5-chloro-2-(1H-tetrazol-1-yl)phenyl)-5-oxo-1,2,3,5-tetrahydroindolizine-3-carboxylic acid (Intermediate 2)

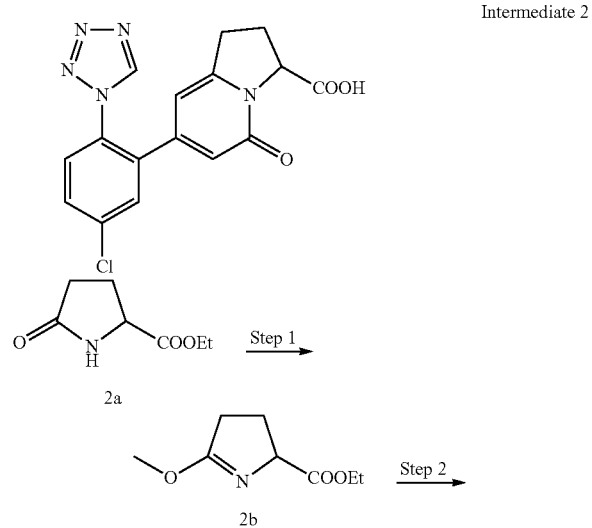

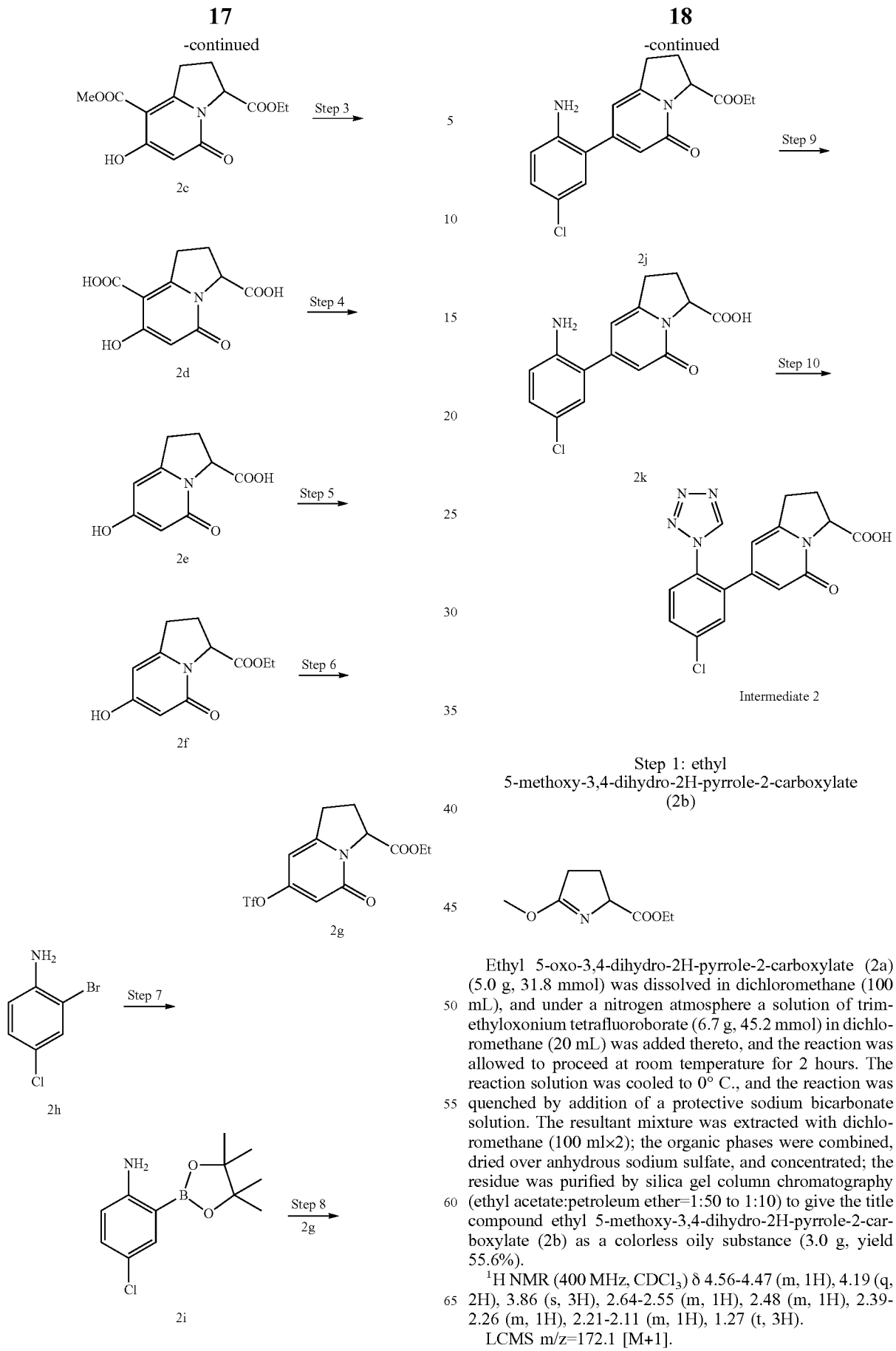

Step 1: ethyl 5-methoxy-3,4-dihydro-2H-pyrrole-2-carboxylate (2b)

Ethyl 5-oxo-3,4-dihydro-2H-pyrrole-2-carboxylate (2a) (5.0 g, 31.8 mmol) was dissolved in dichloromethane (100 mL), and under a nitrogen atmosphere a solution of trimethyloxonium tetrafluoroborate (6.7 g, 45.2 mmol) in dichloromethane (20 mL) was added thereto, and the reaction was allowed to proceed at room temperature for 2 hours. The reaction solution was cooled to 0° C., and the reaction was quenched by addition of a protective sodium bicarbonate solution. The resultant mixture was extracted with dichloromethane (100 ml×2); the organic phases were combined, dried over anhydrous sodium sulfate, and concentrated; the residue was purified by silica gel column chromatography (ethyl acetate:petroleum ether=1:50 to 1:10) to give the title compound ethyl 5-methoxy-3,4-dihydro-2H-pyrrole-2-carboxylate (2b) as a colorless oily substance (3.0 g, yield 55.6%).

$^1$H NMR (400 MHz, CDCl$_3$) δ 4.56-4.47 (m, 1H), 4.19 (q, 2H), 3.86 (s, 3H), 2.64-2.55 (m, 1H), 2.48 (m, 1H), 2.39-2.26 (m, 1H), 2.21-2.11 (m, 1H), 1.27 (t, 3H).

LCMS m/z=172.1 [M+1].

Step 2

3-ethyl 8-methyl 7-hydroxy-5-oxo-1,2,3,5-tetrahydroindolizine-3,8-dicarboxylate (2c)

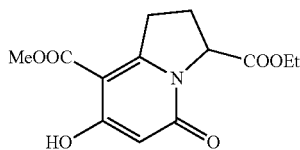 [SMILES: CCOC(=O)C1CCc2c(C(=O)OC)c(O)cc(=O)n21]

Ethyl 5-methoxy-3,4-dihydro-2H-pyrrole-2-carboxylate (2b) (1.0 g, 5.8 mmol) and dimethyl acetone dicarboxylate (1.02 g, 5.8 mmol) were mixed, triethylamine (0.06 mL, 0.4 mmol) was added thereto, and the temperature was raised to 120° C. to allow the reaction to proceed for 3 hours. The reaction solution was separated and purified by silica gel column chromatography (ethyl acetate:petroleum ether=1:10 to 1:2) to give the title compound 3-ethyl 8-methyl 7-hydroxy-5-oxo-1,2,3,5-tetrahydroindolizine-3,8-dicarboxylate (2c) as a light yellow oily substance (1.0 g, yield 63%).
$^1$H NMR (400 MHz, CDCl$_3$) δ 11.29 (s, 1H), 5.83 (s, 1H), 5.13 (dd, 1H), 4.24 (q, 2H), 3.92 (s, 3H), 3.55 (dd, 1H), 3.47 (dd, 1H), 2.49 (dd, 1H), 2.34-2.22 (m, 1H), 1.29 (t, 3H).
LCMS m/z=281.9 [M+1].

Step 3: 7-hydroxy-5-oxo-1,2,3,5-tetrahydroindolizine-3,8-dicarboxylic Acid (2d)

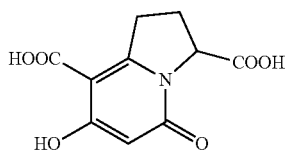 [SMILES: O=C(O)c1c(O)cc(=O)n2c1CCC2C(=O)O]

3-ethyl 8-methyl 7-hydroxy-5-oxo-1,2,3,5-tetrahydroindolizine-3,8-dicarboxylate (2c) (1.0 g, 3.55 mmol) was dissolved in ethanol (5 ml), a solution of NaOH (0.6 g, 14.91 mmol) in water (7.5 mL) was added thereto, and the reaction was allowed to proceed at room temperature overnight. Hydrochloric acid (4 mol/l) was added to the reaction solution to adjust the solution to pH=2. The reaction solution was extracted with dichloromethane (80 ml×3). The organic phases were combined, washed with saturated brine (100 mL), dried over anhydrous sodium sulfate, and concentrated to give the title compound 7-hydroxy-5-oxo-1,2,3,5-tetrahydroindolizine-3,8-dicarboxylic acid (2d) as an off-while solid (0.6 g, yield 71%).
$^1$H NMR (400 MHz, DMSO) δ 5.54 (s, 1H), 4.93 (dd, 1H), 3.61-3.50 (m, 1H), 3.34 (m, 1H), 2.54-2.42 (m, 1H), 2.15 (m, 1H).
LCMS m/z=239.9 [M+1].

Step 4: 7-hydroxy-5-oxo-1,2,3,5-tetrahydroindolizine-3-carboxylic Acid (2e)

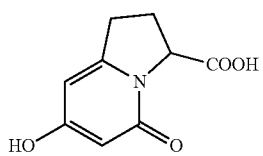 [SMILES: O=C(O)C1CCc2cc(O)cc(=O)n21]

7-hydroxy-5-oxo-1,2,3,5-tetrahydroindolizine-3,8-dicarboxylic acid (2d) (0.5 g, 2.1 mmol) was dissolved in dichloromethane (5 mL), p-toluenesulfonic acid (20.6 mg, 0.12 mmol) was added thereto, and the temperature was raised to 100° C. to allow the reaction to proceed for 4 hours. The reaction solution was concentrated, and the residue was dissolved in dichloromethane and methanol, dried over anhydrous sodium sulfate, and concentrated to give the title compound 7-hydroxy-5-oxo-1,2,3,5-tetrahydroindolizine-3-carboxylic acid (2e) as an off-while solid (0.3 g, yield 73%).
δ (400 MHz, DMSO) 6.20 (s, 1H), 5.93 (s, 1H), 5.07-4.93 (m, 1H), 3.17 (s, 1H), 3.09 (m, 2H), 2.50-2.43 (m, 1H), 2.28-2.12 (m, 1H).
LCMS m/z=195.9 [M+1].

Step 5: ethyl 7-hydroxy-5-oxo-1,2,3,5-tetrahydroindolizine-3-carboxylate (2f)

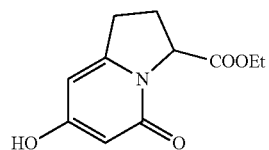 [SMILES: CCOC(=O)C1CCc2cc(O)cc(=O)n21]

7-hydroxy-5-oxo-1,2,3,5-tetrahydroindolizine-3-carboxylic acid (2e) (0.3 g, 1.5 mmol) was dissolved in ethanol (20 mL), concentrated sulfuric acid (0.2 mL) was added thereto, and the temperature was raised to 100° C. to allow the reaction to proceed for 4 hours. The reaction solution was separated and purified by silica gel column chromatography (dichloromethane:methanol=100:1 to 10:1 to give the title compound ethyl 7-hydroxy-5-oxo-1,2,3,5-tetrahydroindolizine-3-carboxylate (2f) as a light yellow oily substance (480 mg, yield>100%).
$^1$H NMR (400 MHz, CDCl$_3$) δ 10.10 (s, 1H), 6.65 (s, 1H), 6.58 (s, 1H), 5.28 (m, 1H), 4.13 (q, 2H), 3.24 (m, 2H), 2.76 (m, 1H), 2.41 (m, 1H), 1.33 (t, 3H).
LCMS m/z=224.0 [M+1].

Step 6: ethyl 5-oxo-7-(((trifluoromethyl)sulfonyl)oxy)-1,2,3,5-tetrahydroindolizine-3-carboxylate (2g)

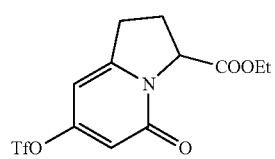 [SMILES: CCOC(=O)C1CCc2cc(OS(=O)(=O)C(F)(F)F)cc(=O)n21]

Ethyl 7-hydroxy-5-oxo-1,2,3,5-tetrahydroindolizine-3-carboxylate (2f) (480 mg, 2.1 mmol) was dissolved in N,N-dimethylformamide (10 mL), triethylamine (0.6 mL, 4.6 mmol) and N-phenyl-p-bis(trifluoromethanesulfonimide) (900 mg, 2.5 mmol) were added thereto, and the reaction was allowed to proceed at room temperature for 1 hour. Ethyl acetate (100 mL) was added to the reaction solution, which was washed with water (60 mL×3) and then saturated brine (60 mL), dried over anhydrous sodium sulfate, and concentrated; the residue was purified by silica gel column chromatography (ethyl acetate:petroleum ether=1:10 to 1:2) to give the title compound ethyl 5-oxo- 7-(((trifluoromethyl)sulfonyl)oxy)-1,2,3,5-tetrahydroindolizine-3-carboxylate (2g) as a yellow oily substance (0.4 g, yield 54%).

$^1$H NMR (400 MHz, CDCl$_3$) δ 6.31 (d, 1H), 6.15 (d, 1H), 5.10 (dd, 1H), 4.23 (q, 2H), 3.24 (m, 1H), 3.12 (m, 1H), 2.57 (m, 1H), 2.35 (m, 1H), 1.30 (t, 3H).

LCMS m/z=355.8 [M+1].

Step 7: 4-chloro-2-(4,4,5,5-tetramethyl-1,3,2-dioxaborolan-2-yl)aniline (2i)

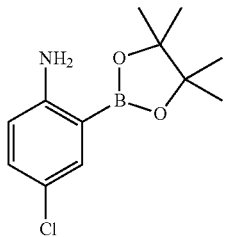 [SMILES: CC1(C)OB(c2cc(Cl)ccc2N)OC1(C)C]

4-chloro-2-bromo-aniline (206 mg, 0.01 mmol) was dissolved in dimethylsulfoxide (20 mL). Under a nitrogen atmosphere, bis(pinacolato)diboron (3.8 g, 15 mmol), potassium acetate (2.5 g, 25.7 mmol) and [1,1'-bis(diphenylphosphino)ferrocene] dichloropalladium (218 mg, 0.3 mmol) were added thereto, and the temperature was raised to 80° C. to allow the reaction to proceed for 24 hours. Water (100 ml) was added to the reaction solution, which was extracted with ethyl acetate (80 ml×2). The organic phases were combined, washed with saturated brine (100 mL), dried over anhydrous sodium sulfate, and concentrated. The residue was purified by silica gel column chromatography (ethyl acetate:petroleum ether=1:100 to 1:30) to give the title compound 4-chloro-2-(4,4,5,5-tetramethyl-1,3,2-dioxaborolan-2-yl)aniline (2i) as a white solid (2.0 g, yield 79%).

$^1$H NMR (400 MHz, CDCl$_3$) δ 7.54 (s, 1H), 7.19-7.08 (m, 1H), 6.55 (d, 1H), 4.86 (s, 2H), 1.34 (s, 12H).

LCMS m/z=254.0 [M+1].

Step 8: ethyl 7-(2-amino-5-chlorophenyl)-5-oxo-1,2,3,5-tetrahydroindolizine-3-carboxylate (2j)

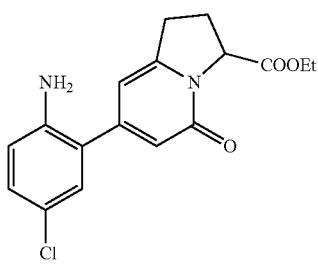 [SMILES: CCOC(=O)C1CCc2cc(-c3cc(Cl)ccc3N)cc(=O)n21]

Ethyl 5-oxo-7-(((trifluoromethyl)sulfonyl)oxy)-1,2,3,5-tetrahydroindolizine-3-carboxylate (2g) (355 mg, 0.1 mmol) and 4-chloro-2-(4,4,5,5-tetramethyl-1,3,2-dioxaborolan-2-yl)aniline (2i) (253 g, 0.1 mmol) were dissolved in 1,4-dioxane (30 mL). Under a nitrogen atmosphere, cesium fluoride (380 mg, 0.25 mmol) and tetrakis(triphenylphosphine)palladium (28.9 mg, 0.025 mmol) were added thereto, and the temperature was raised to 105° C. to allow the reaction to proceed for 1 hour. Ethyl acetate (100 mL) was added to the reaction solution, which was washed with water (50 mL×2) and then saturated brine (50 mL), dried over anhydrous sodium sulfate, and concentrated; the residue was purified by silica gel column chromatography (ethyl acetate: petroleum ether=1:20 to 1:1) to give the title compound 7-(2-amino-5-chlorophenyl)-5-oxo-1,2,3,5-tetrahydroindolizine-3-carboxylate (2j) as a light yellow solid (120 g, yield 36%).

$^1$H NMR (400 MHz, CDCl$_3$) δ 7.11 (dd, 1H), 7.08 (d, 1H), 6.67 (d, 1H), 6.50 (s, 1H), 6.23 (s, 1H), 5.16 (dd, 1H), 4.27 (q, 2H), 3.51 (s, 2H), 3.23 (m, 1H), 3.12 (m, 1H), 2.54 (m, 1H), 2.39-2.27 (m, 1H), 1.31 (t, 3H).

LCMS m/z=332.9 [M+1].

Step 9: 7-(2-amino-5-chlorophenyl)-5-oxo-1,2,3,5-tetrahydroindolizine-3-carboxylic Acid (2k)

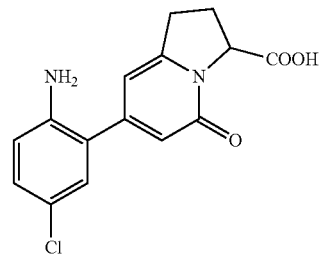 [SMILES: Nc1ccc(Cl)cc1-c1cc2n(c(=O)c1)C(C(=O)O)CC2]

Ethyl 7-(2-amino-5-chlorophenyl)-5-oxo-1,2,3,5-tetrahydroindolizine-3-carboxylate (2j) (600 mg, 1.8 mmol) was dissolved in ethanol (10 mL), sodium hydroxide (288 mg, 7.2 mmol) was added thereto, and the reaction was allowed to proceed at room temperature for 4 hours. A hydrochloric acid solution (4 mol/L) was added to the reaction solution to adjust it to pH=3 to 4. The reaction solution was extracted with dichloromethane (60 ml×3). The organic phases were combined, washed with saturated brine (60 mL), dried over anhydrous sodium sulfate, concentrated, and recrystallized to give the title compound 7-(2-amino-5-chlorophenyl)-5-oxo-1,2,3,5-tetrahydroindolizine-3-carboxylic acid (2k) as a yellow solid (400 mg, yield 73%).

$^1$H NMR (400 MHz, DMSO) δ 7.16 (dd, 1H), 7.09 (d, 1H), 6.86 (d, 1H), 6.29 (d, 1H), 6.25 (d, 1H), 4.92 (dd, 1H), 3.11 (m, 2H), 2.50-2.45 (m, 1H), 2.27-2.14 (m, 1H).

LCMS m/z=304.9 [M+1].

Step 10

7-(5-chloro-2-(1H-tetrazol-1-yl)phenyl)-5-oxo-1,2,3,5-tetrahydroindolizine-3-carboxylic Acid (Intermediate 2)

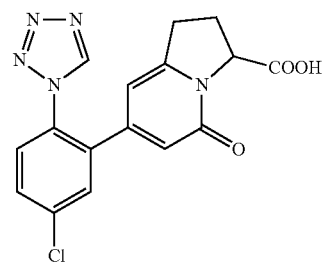 [SMILES: O=C(O)C1CCc2cc(-c3cc(Cl)ccc3-n3cnnn3)cc(=O)n21]

7-(2-amino-5-chlorophenyl)-5-oxo-1,2,3,5-tetrahydroindolizine-3-carboxylic acid (2k) (400 mg, 1.3 mmol) was dissolved in acetic acid (5 mL), trimethyl orthoformate (414 mg, 3.9 mmol) and sodium azide (214.5 g, 3.9 mmol) were added thereto, the reaction was allowed to proceed at room temperature for half an hour, and further for 2 hours at 75° C. The reaction solution was cooled to room temperature, water (100 ml) was added thereto, and the reaction solution was extracted with dichloromethane (60 ml×3). The organic phases were combined, washed with saturated brine (60 ml×2), dried over anhydrous sodium sulfate, and concentrated to give the title compound 7-(5-chloro-2-(1H-tetrazol-1-yl)phenyl)-5-oxo-1,2,3,5-tetrahydroindolizine-3-carboxylic acid (Intermediate 2) as a yellow solid (400 mg, yield 86%).

$^1$H NMR (400 MHz, DMSO) δ 9.68 (s, 1H), 7.80 (m, 2H), 7.79-7.76 (m, 1H), 5.97 (d, 1H), 5.90 (d, 1H), 4.85 (dd, 1H), 2.97 (m, 2H), 2.44 (m, 1H), 2.19-2.05 (m, 1H).

LCMS m/z=357.8 [M+1].

Intermediate 3

2-(4-(5-chloro-2-(1H-tetrazol-1-yl)phenyl))-2-oxopyridin-1-yl)acetic Acid (Intermediate 3)

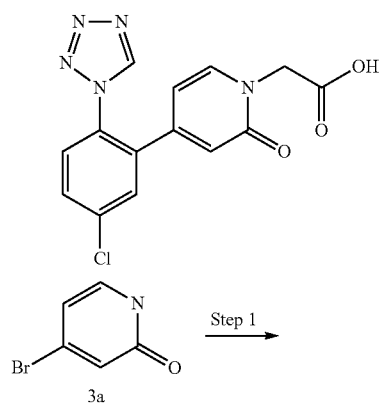

Intermediate 3

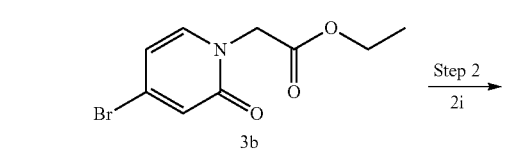

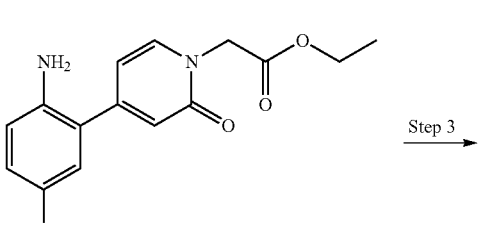

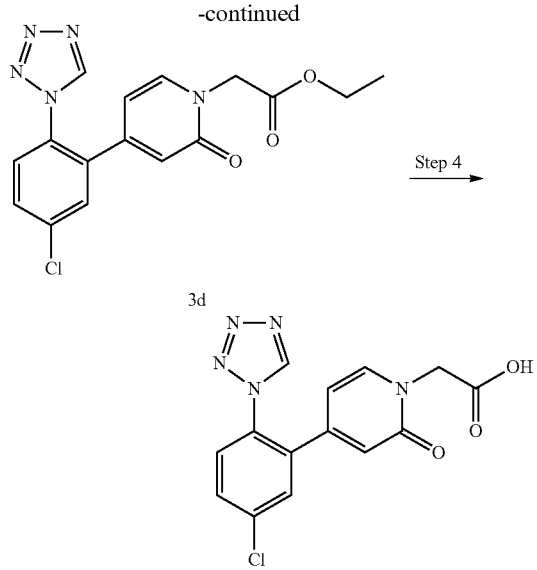

Step 1: ethyl 2-(4-bromo-2-oxo-pyridin-1(2H)-yl)acetate (3b)

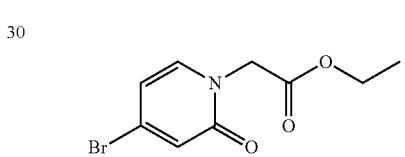

4-bromopyridin-2-one (1 g, 5.7 mmol), bromoethyl acetate (1.06 g, 6.3 mmol) and potassium carbonate (0.95 g, 6.9 mmol) were dissolved in N,N-dimethylformamide (20 mL), and allowed to react overnight at room temperature. The reaction solution was introduced into water (50 mL) and extracted with ethyl acetate (50 mL×2). The organic phases were combined, dried over anhydrous sodium sulfate, and concentrated to obtain the title compound ethyl 2-(4-bromo-2-oxo-pyridin-1(2H)-yl)acetate (3b) as a white solid (1.5 g, yield 100%).

$^1$H NMR (400 MHz, CDCl$_3$) δ 7.09 (d, 1H), 6.86 (d, 1H), 6.37 (dd, 1H), 4.60 (s, 2H), 4.25 (q, 2H), 1.45-1.11 (m, 3H).
LCMS m/z=260.0 [M+1].

Step 2: ethyl 2-(4-(5-chloro-2-aminophenyl)-2-oxopyridin-1(2H)-yl)acetate (3c)

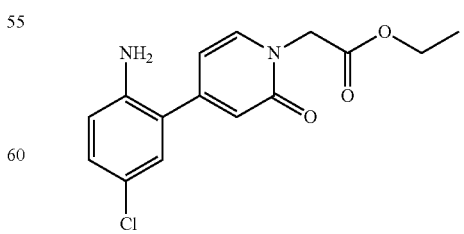

4-chloro-2-(4,4,5,5-tetramethyl-1,3,2-dioxaborolan-2-yl)aniline (2i) (0.1 g, 0.39 mmol), ethyl 2-(4-bromo-2-oxo-pyridin-1(2H)-yl)acetate (0.15 g, 0.59 mmol) and an aqueous solution of sodium bicarbonate (2 mL, 0.39 mmol) were dissolved in dioxane (10 mL), and the temperature was raised to 110° C. to allow the reaction to proceed overnight. Water (50 ml) was added to the reaction solution, which was extracted with ethyl acetate (50 ml×3). The organic phases were combined, dried over anhydrous sodium sulfate, and concentrated. The residue was purified by silica gel column chromatography (petroleum ether:ethyl acetate=1:1) to give the title compound ethyl 2-(4-(5-chloro-2-aminophenyl)-2-oxo-pyridin-1(2H)-yl)acetate (3c) as a white solid (13 mg, yield 11%).

$^1$H NMR (400 MHz, DMSO) δ 7.71 (d, 1H), 7.12 (dd, 1H), 7.06 (d, 1H), 6.77 (d, 1H), 6.45 (d, 1H), 6.35 (dd, 1H), 5.20 (s, 2H), 4.71 (s, 2H), 4.16 (q, 2H), 1.23 (t, 3H).

LCMS m/z=307.1 [M+1].

Step 3: ethyl 2-(4-(5-chloro-2-(1H-tetrazol-1-yl)phenyl))-2-oxo-pyridin-1-yl)acetate (3d)

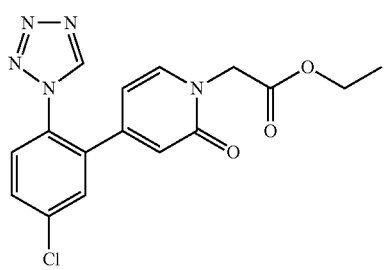 [SMILES: CCOC(=O)Cn1ccc(-c2cc(Cl)ccc2-n2cnnn2)cc1=O]

Ethyl 2-(4-(5-chloro-2-aminophenyl)-2-oxo-pyridin-1(2H)-yl)acetate (3c) (0.05 g, 0.16 mmol) and trimethyl orthoformate (51.9 mg, 0.49 mmol) were dissolved in acetic acid (10 mL), and allowed to react at room temperature for 10 min. Sodium azide (31.8 g, 0.49 mmol) was added thereto, and the temperature was raised to 80° C. to allow reaction to proceed overnight. Water (50 ml) was added to the reaction solution, which was extracted with ethyl acetate (50 ml×3). The organic phases were combined, dried over anhydrous sodium sulfate, and concentrated to give the title compound ethyl 2-(4-(5-chloro-2-(H-tetrazol-1-yl)phenyl))-2-oxo-pyridin-1-yl)acetate (3d) as a white solid (46 mg, yield 80%).

$^1$H NMR (400 MHz, DMSO) δ 9.68 (s, 1H), 7.92-7.75 (m, 3H), 7.57 (d, 1H), 6.30 (d, 1H), 5.84 (dd, 1H), 4.64 (s, 2H), 4.13 (q, 2H), 1.20 (t, 3H).

LCMS m/z=360.1 [M+1].

Step 4: 2-(4-(5-chloro-2-(1H-tetrazol-1-yl)phenyl))-2-oxo-pyridin-1-yl)acetic Acid (Intermediate 3)

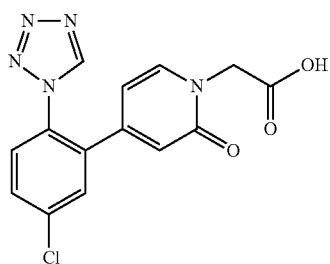 [SMILES: O=C(O)Cn1ccc(-c2cc(Cl)ccc2-n2cnnn2)cc1=O]

Ethyl 2-(4-(5-chloro-2-(1H-tetrazol-1-yl)phenyl))-2-oxo-pyridin-1-yl)acetate (3d) (0.37 g, 1.0 mmol) was dissolved in tetrahydrofuran (10 mL), and lithium hydroxide (0.17 g, 4.12 mmol) was added thereto, followed by reaction at room temperature for 2 hours. The reaction solution was added to water (10 mL), adjusted to pH=2 with hydrochloric acid (4 mol/L), and extracted with ethyl acetate (10 ml×2). The organic phases were combined, dried over anhydrous sodium sulfate, and concentrated to give the title compound 2-(4-(5-chloro-2-(1H-tetrazol-1-yl)phenyl))-2-oxo-pyridin-1-yl)acetic acid (intermediate 3) as a yellow solid (0.2 g, yield 58%).

$^1$H NMR (400 MHz, DMSO) δ 9.69 (s, 1H), 7.88-7.72 (m, 3H), 7.56 (d, 1H), 6.28 (d, 1H), 5.81 (dd, 1H), 4.56 (s, 2H).

LCMS m/z=332.0 [M+1].

Example 1

N-(4-carboxyphenyl)-2-(5-chloro-2-(1H-tetrazol-1-yl)phenyl)-4-oxo-4,6,7,8-tetrahydropyrrolo[1,2-a]pyrimidine-6-carboxamide (Compound 1)

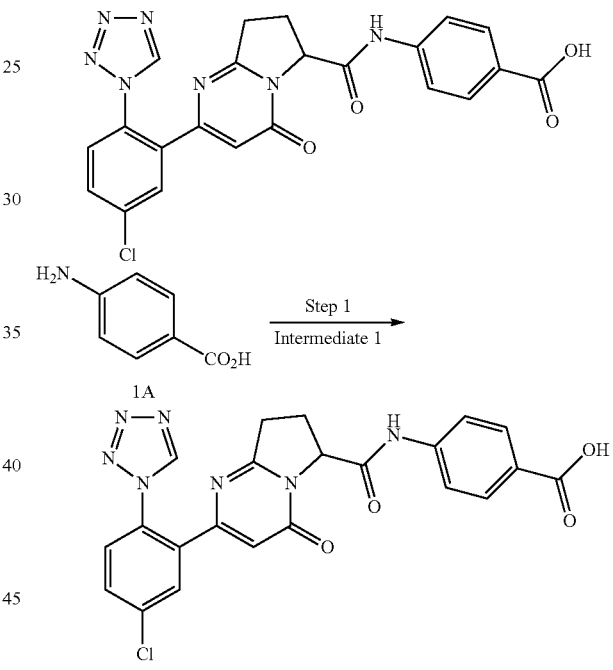

Compound 1

Step 1

N-(4-carboxyphenyl)-2-(5-chloro-2-(1H-tetrazol-1-yl)phenyl)-4-oxo-4,6,7,8-tetrahydropyrrolo[1,2-a]pyrimidine-6-carboxamide (Compound 1)

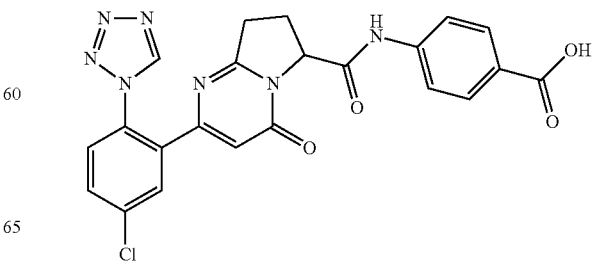

2-(5-chloro-2-(1H-tetrazol-1-yl)phenyl)-4-oxo-4,6,7,8-tetrahydropyrrolo[1,2-a]pyrimidine-6-carboxylic acid (Intermediate 1) (130 mg, 0.36 mmol) was dissolved in tetrahydrofuran (6 ml), and under a protective nitrogen atmosphere, the solution was cooled to 0° C., a solution of oxalyl chloride (137 mg, 1.08 mmol) in N,N-dimethylformamide (2 drops) was added dropwise thereto, and the reaction was allowed to proceed at room temperature for 2 hours, then tetrahydrofuran was removed under reduced pressure to obtain reaction liquid 1; p-aminobenzoic acid (60 mg, 0.43 mmol) was dissolved in tetrahydrofuran (5 ml), triethylamine (109.3 mg, 108 mmol) and reaction liquid 1 prepared above were added thereto, and the reaction was allowed to proceed for 3 hours at room temperature. Water (10 ml) was added to the reaction solution to quench the reaction, and the reaction solution was extracted with ethyl acetate (10 ml×2). The organic phases were combined, dried over anhydrous sodium sulfate, and concentrated. The residue was purified by silica gel column chromatography (dichloromethane:methanol=49:1 to 9:1) to give the title compound N-(4-carboxyphenyl)-2-(5-chloro-2-(1H-tetrazol-1-yl)phenyl)-4-oxo-4,6,7,8-tetrahydropyrrolo[1,2-a]pyrimidine-6-carboxamide (Compound 1) as a light gray solid (30 mg, yield 17%).

$^1$H NMR (400 MHz, DMSO) δ 12.50 (s, 1H), 10.94 (s, 1H), 9.73 (s, 1H), 7.98 (d, 1H), 7.86 (m, 4H), 7.72 (d, 2H), 6.38 (s, 1H), 5.17 (dd, 1H), 2.93 (m, 1H), 2.79 (m, 1H), 2.54 (m, 1H), 2.15 (m, 1H).

LCMS m/z=477.8 [M+1].

Example 2

N-(4-carboxyphenyl)-7-(5-chloro-2-(H-tetrazol-1-yl)phenyl)-5-oxo-1,2,3,5-tetrahydroindolizine-3-carboxamide (Compound 2)

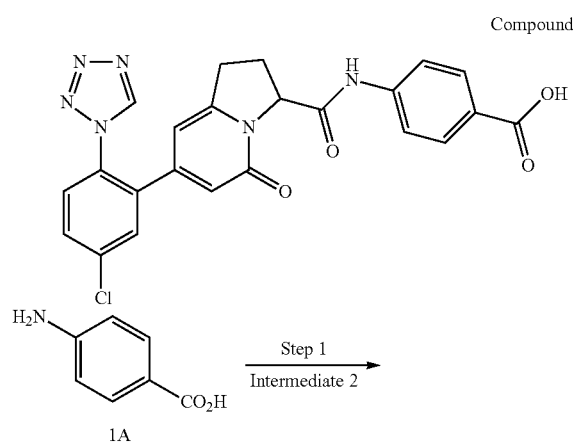

Step 1

N-(4-carboxyphenyl)-7-(5-chloro-2-(1H-tetrazol-1-yl)phenyl)-5-oxo-1,2,3,5-tetrahydroindolizine-3-carboxamide (Compound 2)

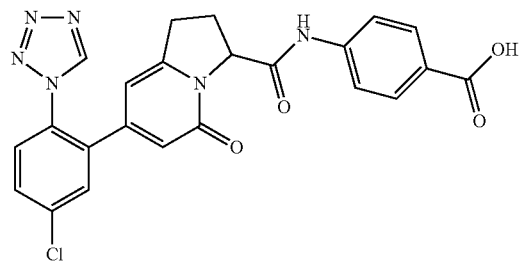 [SMILES: O=C(O)c1ccc(NC(=O)C2CCc3cc(-c4cc(Cl)ccc4-n4cnnn4)cc(=O)n32)cc1]

7-(5-chloro-2-(1H-tetrazol-1-yl)phenyl)-5-oxo-1,2,3,5-tetrahydroindolizine-3-carboxylic acid (Intermediate 2) (100 mg, 0.28 mmol) was dissolved in tetrahydrofuran (10 ml), and under a protective nitrogen atmosphere, the solution was cooled to 0° C., a solution of oxalyl chloride (0.07 ml, 0.84 mmol) in N,N-dimethylformamide (2 drops) was added dropwise thereto, and the reaction was allowed to proceed for 2 hours at room temperature. Tetrahydrofuran was removed under reduced pressure to obtain reaction liquid 1; p-aminobenzoic acid (46 mg, 0.33 mmol) was dissolved in tetrahydrofuran (5 ml), triethylamine (85 mg, 0.84 mmol) and reaction liquid 1 prepared above were added thereto, and the reaction was allowed to proceed for 1 hour at room temperature. Water (80 ml) was added to the reaction solution, which was extracted with ethyl acetate (80 ml×2). The organic phases were combined, washed with saturated brine (80 mL), dried over anhydrous sodium sulfate, and concentrated. The residue was purified by silica gel column chromatography (dichloromethane:methanol=100:1 to 100:3) to give the title compound N-(4-carboxyphenyl)-7-(5-chloro-2-(1H-tetrazol-1-yl)phenyl)-5-oxo-1,2,3,5-tetrahydroindolizine-3-carboxamide (Compound 2) as a light yellow solid (35 mg, yield 26%).

$^1$H NMR (400 MHz, DMSO) δ 12.72 (s, 1H), 10.74 (s, 1H), 9.69 (s, 1H), 7.90 (d, 2H), 7.80 (m, 3H), 7.70 (d, 2H), 5.99 (s, 1H), 5.94 (s, 1H), 5.11 (dd, 1H), 3.16-2.90 (m, 3H), 2.18 (m, 1H).

LCMS m/z=476.8 [M+1].

Example 3

N-(2-carboxyindol-5-yl)-7-(5-chloro-2-(1H-tetrazol-1-yl)phenyl)-5-oxo-1,2,3,5-tetrahydroindolizine-3-carboxamide (Compound 3)

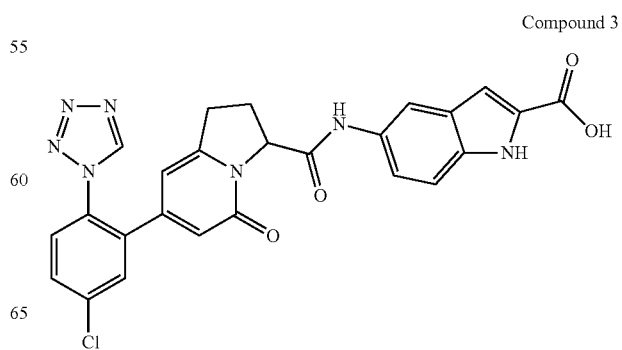

29

-continued

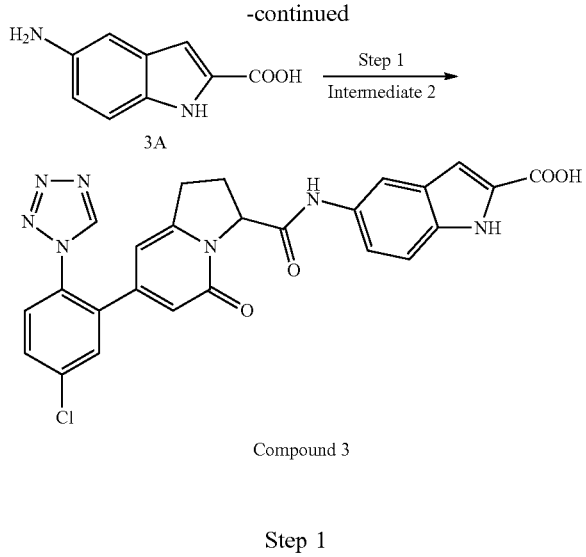

Compound 3

Step 1

N-(2-carboxyindol-5-yl)-7-(5-chloro-2-(1H-tetrazol-1-yl)phenyl)-5-oxo-1,2,3,5-tetrahydroindolizine-3-carboxamide (Compound 3)

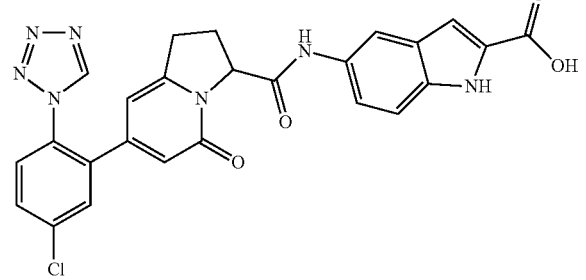

7-(5-chloro-2-(1H-tetrazol-1-yl)phenyl)-5-oxo-1,2,3,5-tetrahydroindolizine-3-carboxylic acid (Intermediate 2) (100 mg, 0.28 mmol) was dissolved in tetrahydrofuran (10 ml), and under a protective nitrogen atmosphere, the solution was cooled to 0° C., a solution of oxalyl chloride (0.07 ml, 0.84 mmol) in N,N-dimethylformamide (2 drops) was added dropwise thereto, and the reaction was allowed to proceed for 2 hours at room temperature, to obtain reaction liquid 1; 5-aminoindole-2-carboxylic acid (59.2 mg, 0.34 mmol) was dissolved in tetrahydrofuran (10 ml), triethylamine (85 mg, 0.84 mmol) was added thereto, the solution pH was adjusted to 9 to 10, reaction liquid 1 prepared above was added, and the reaction was allowed to proceed for 2 hours at room temperature. Dilute hydrochloric acid at 4 mol/l was added to the reaction solution to adjust the solution to pH=4, and the solution was extracted with ethyl acetate (80 ml×2). The organic phases were combined, washed with saturated brine (100 mL), dried over anhydrous sodium sulfate, and concentrated. The residue was purified by silica gel column chromatography (dichloromethane:methanol=100:1 to 20:1) to give the title compound N-(2-carboxyindol-5-yl)-7-(5-chloro-2-(1H-tetrazol-1-yl)phenyl)-5-oxo-1,2,3,5-tetrahydroindolizine-3-carboxamide (Compound 3) as a khaki solid (10 mg, yield 7%).

$^1$H NMR (400 MHz, DMSO) δ 11.69 (s, 1H), 10.31 (s, 1H), 9.69 (s, 1H), 8.00 (s, 1H), 7.80 (d, 3H), 7.36 (m, 2H), 7.03 (s, 1H), 5.98 (s, 1H), 5.93 (s, 1H), 5.11 (dd, 1H), 3.03 (m, 3H), 2.18 (m, 1H).

LCMS m/z=515.8 [M+1].

30

Example 4

N-(2-carboxyindol-5-yl)-2-(5-chloro-2-(1H-tetrazol-1-yl)phenyl)-4-oxo-4,6,7,8-tetrahydropyrrolo[1,2-a]pyrimidine-6-carboxamide (Compound 4)

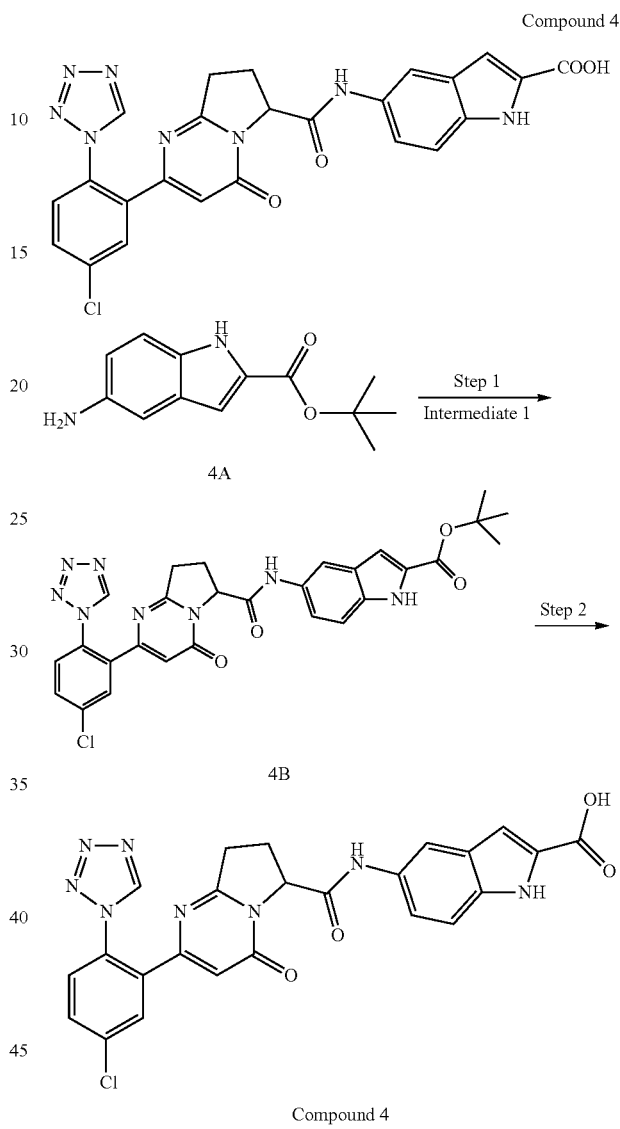

Step 1

N-(2-tert-butoxycarbonylindol-5-yl)-2-(5-chloro-2-(1H-tetrazol-1-yl)phenyl)-4-oxo-4,6,7,8-tetrahydropyrrolo[1,2-a]pyrimidine-6-carboxamide (4B)

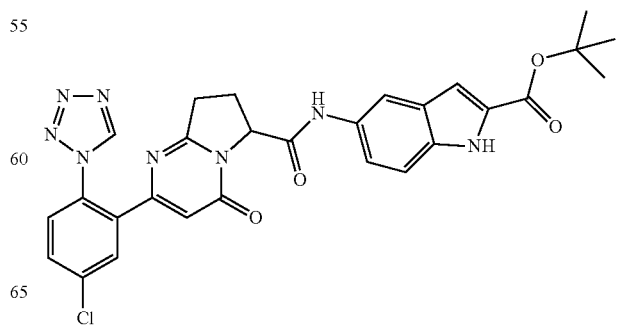

2-(5-chloro-2-(1H-tetrazol-1-yl)phenyl)-4-oxo-4,6,7,8-tetrahydropyrrolo[1,2-a]pyrimidine-6-carboxylic acid (Intermediate 1) (100 mg, 0.28 mmol) was dissolved in tetrahydrofuran (5 ml) and cooled to 0° C. Under a protective nitrogen atmosphere, oxalyl chloride (107 mg, 0.84 mmol) and N,N-dimethylformamide (2 drops) were added dropwise thereto, the temperature was raised to room temperature at which the reaction was allowed to proceed for 2 hours. The solvent was removed under reduced pressure, tetrahydrofuran (5 ml) was added to the residue, the solution was cooled to 0° C., a solution of t-butyl 5-aminoindole-2-carboxylate (79.2 mg, 0.34 mmol) in tetrahydrofuran (3 ml) was added dropwise thereto, and the reaction was allowed to proceed for 3 hours at room temperature. Water (10 ml) was added to the reaction solution to quench the reaction, and the reaction solution was extracted with ethyl acetate (10 ml×3). The organic phases were combined, dried over anhydrous sodium sulfate, and concentrated. The residue was purified by silica gel column chromatography (dichloromethane:methanol=49:1 to 9:1) to give the title compound N-(2-tert-butoxycarbonylindol-5-yl)-2-(5-chloro-2-(1H-tetrazol-1-yl)phenyl)-4-oxo-4,6,7,8-tetrahydropyrrolo[1,2-a]pyrimidine-6-carboxamide (4B) as a light yellow solid (80 mg, yield 50%).

Step 2

N-(2-carboxyindol-5-yl)-2-(5-chloro-2-(1H-tetrazol-1-yl)phenyl)-4-oxo-4,6,7,8-tetrahydropyrrolo[1,2-a]pyrimidine-6-carboxamide (Compound 4)

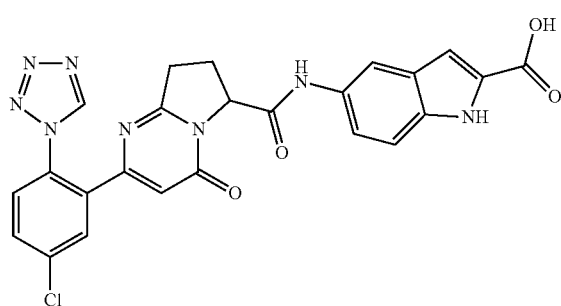 [SMILES: O=C(O)c1cc2cc(NC(=O)C3CCc4nc(-c5cc(Cl)ccc5-n5cnnn5)cc(=O)n43)ccc2[nH]1]

N-(2-tert-butoxycarbonylindol-5-yl)-2-(5-chloro-2-(1H-tetrazol-1-yl)phenyl)-4-oxo-4,6,7,8-tetrahydropyrrolo[1,2-a]pyrimidine-6-carboxamide (4B) (80 mg, 0.14 mmol) was dissolved in tetrahydrofuran (5 ml), trifluoroacetic acid (638 mg, 5.6 mmol) was added thereto, and the temperature was raised to 80° C. to allow the reaction to proceed for 4 hours. Water (10 ml) was added to the reaction solution to quench the reaction, and the reaction solution was extracted with ethyl acetate (10 ml×3). The organic phases were combined, dried over anhydrous sodium sulfate, and concentrated. The residue was purified by silica gel column chromatography (dichloromethane:methanol=49:1 to 9:1) to give the title compound N-(2-carboxyindol-5-yl)-2-(5-chloro-2-(1H-tetrazol-1-yl)phenyl)-4-oxo-4,6,7,8-tetrahydropyrrolo[1,2-a]pyrimidine-6-carboxamide (Compound 4) as a light yellow solid (46 mg, yield 64%).

$^1$H NMR (400 MHz, DMSO) δ 11.19 (s, 1H), 10.39 (s, 1H), 9.74 (s, 1H), 7.98 (d, 1H), 7.81-7.90 (m, 3H), 7.29 (dd, 2H), 6.74 (s, 1H), 6.37 (s, 1H), 5.16 (d, 1H), 2.99-2.90 (m, 1H), 2.80-2.74 (m, 1H), 2.49-2.46 (m, 1H), 2.16-2.11 (m, 1H).

LCMS m/z=517.1 [M+1].

Example 5

N-(4-carboxyphenyl)-2-(4-(5-chloro-2-(1H-tetrazol-1-yl)phenyl))-2-oxo-pyridin-1-yl)acetamide (Compound 5)

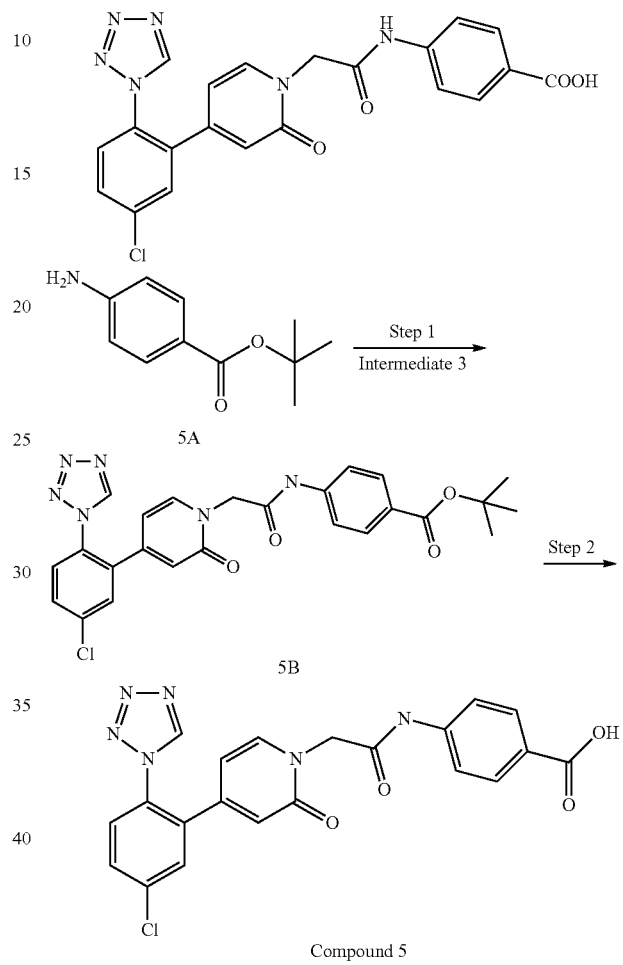

Step 1

N-(4-tert-butoxycarboxylphenyl)-2-(4-(5-chloro-2-(1H-tetrazol-1-yl)phenyl))-2-oxo-pyridin-1-yl)acetamide (5B)

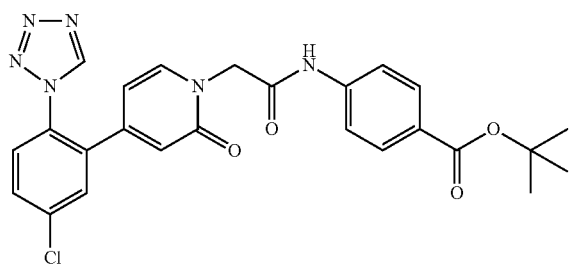 [SMILES: CC(C)(C)OC(=O)c1ccc(NC(=O)Cn2ccc(-c3cc(Cl)ccc3-n3cnnn3)cc2=O)cc1]

2-(4-(5-chloro-2-(1H-tetrazol-1-yl)phenyl))-2-oxo-pyridin-1-yl)acetic acid (Intermediate 3) (0.15 g, 0.45 white sol) and t-butyl p-aminobenzoate (0.34 g, 1.8 mmol) were dissolved in pyridine (20 ml), and 1-(3-dimethylaminopropyl)-3-ethyl-carbodiimide (0.69 g, 3.6 mmol) was added thereto, and the reaction was allowed to proceed at room temperature for 4 hours. The reaction solution was added to water (50 mL) and extracted with ethyl acetate (50 mL×2). The organic phases were combined, dried over anhydrous sodium sulfate, and concentrated to obtain the title compound N-(4-tert-butoxycarboxylphenyl)-2-(4-(5-chloro-2-(1H-tetrazol-1-yl)phenyl))-2-oxo-pyridin-1-yl)acetamide (5B) as a white solid (175 mg, yield 77%).

$^1$H NMR (400 MHz, DMSO) δ 10.66 (s, 1H), 9.70 (s, 1H), 7.86 (d, 2H), 7.82 (m, 3H), 7.68 (d, 2H), 7.58 (d, 1H), 6.29 (d, 1H), 5.84 (dd, 1H), 4.74 (s, 2H), 1.53 (s, 9H).

LCMS m/z=507.3 [M+1].

Step 2

N-(4-carboxyphenyl)-2-(4-(5-chloro-2-(1H-tetrazol-1-yl)phenyl))-2-oxo-pyridin-1-yl)acetamide (Compound 5)

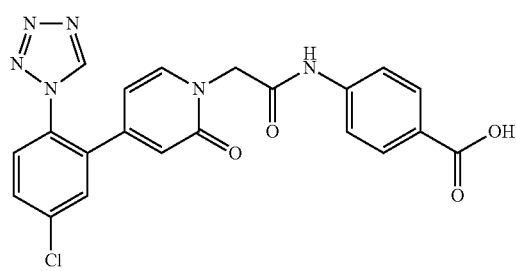 [SMILES: O=C(Cn1ccc(-c2cc(Cl)ccc2-n2cnnn2)cc1=O)Nc1ccc(C(=O)O)cc1]

N-(4-tert-butoxycarboxylphenyl)-2-(4-(5-chloro-2-(1H-tetrazol-1-yl)phenyl))-2-oxo-pyridin-1-yl)acetamide (5B) (170 mg, 0.33 mmol) was dissolved in dichloromethane (5 mL), trifluoroacetic acid (0.5 ml, 6.6 mmol) was added thereto, and the reaction was allowed to proceed at room temperature for 2 hours. Trifluoroacetic acid was removed under reduced pressure from the reaction solution, and the residue was dissolved with dichloromethane, water (20 ml) was added thereto, and the solution pH was adjusted to 6 to 7 with a saturated sodium bicarbonate solution, followed by washing with saturated brine (20 ml×3), drying over anhydrous sodium sulfate, and concentration, to give the title compound N-(4-carboxyphenyl)-2-(4-(5-chloro-2-(1H-tetrazol-1-yl)phenyl))-2-oxo-pyridin-1-yl)acetamide (Compound 5) as an off-white solid (80 mg, yield 54%).

$^1$H NMR (400 MHz, DMSO) δ 12.69 (s, 1H), 10.72 (s, 1H), 9.71 (s, 1H), 7.90 (d, 2H), 7.85-7.79 (m, 3H), 7.69 (d, 2H), 7.59 (d, 1H), 6.30 (d, 1H), 5.84 (dd, 1H), 4.75 (s, 2H).

LCMS m/z=451.1 [M+1].

Example 6

N-(2-carboxyindol-5-yl)-2-(4-(5-chloro-2-(1H-tetrazol-1-yl)phenyl))-2-oxo-pyridin-1-yl)acetamide (Compound 6)

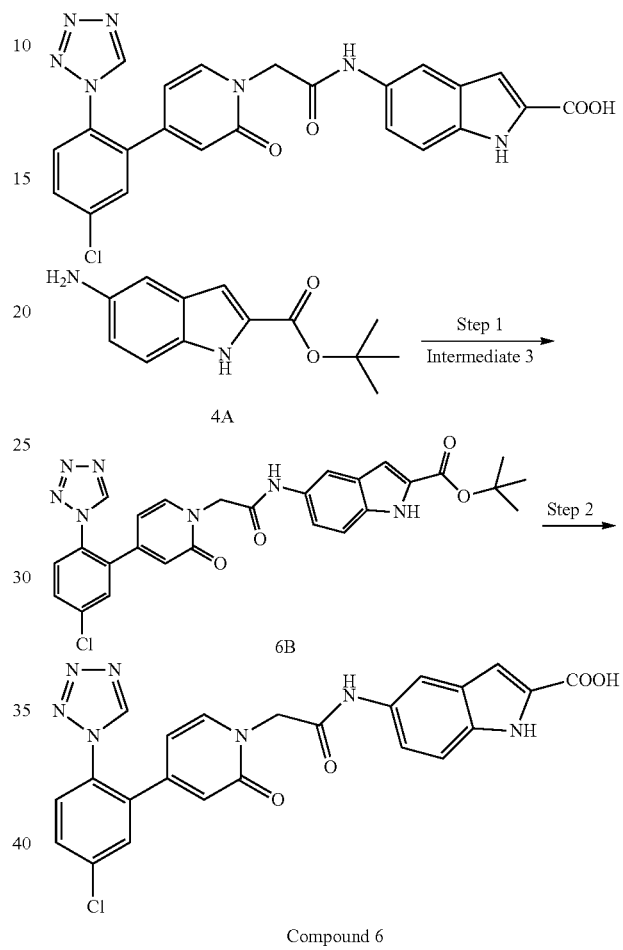

Step 1

N-(2-tert-butoxycarboxylindol-5-yl)-2-(4-(5-chloro-2-(1H-tetrazol-1-yl)phenyl))-2-oxo-pyridin-1-yl)acetamide (6B)

2-(4-(5-chloro-2-(1H-tetrazol-1-yl)phenyl))-2-oxo-pyridin-1-yl)acetic acid (Intermediate 3) (0.2 g, 0.6 mmol), t-butyl 5-aminoindole-2-carboxylate (174 mg, 0.72 mmol) and 1-(3-dimethylaminopropyl)-3-ethyl-carbodiimide (460 mg, 2.4 mmol) were added in pyridine (10 mL), and allowed to react at room temperature for 2 hours. The reaction solution was added to water (50 ml), adjusted to pH=2 with hydrochloric acid (6 mol/L), and extracted with ethyl acetate (20 ml×2); the organic phases were combined, dried over anhydrous sodium sulfate, and concentrated; the residue was purified by silica gel column chromatography (dichloromethane:methanol=50:1) to give the title compound N-(2-tert-butoxycarboxylindol-5-yl)-2-(4-(5-chloro-2-(1H-tetrazol-1-yl)phenyl))-2-oxo-pyridin-1-yl)acetamide (6B) as a red solid (170 mg, yield 85%).

¹H NMR (400 MHz, DMSO) δ 11.61 (s, 1H), 10.21 (s, 1H), 9.70 (s, 1H), 7.96 (d, 1H), 7.91-7.75 (m, 3H), 7.59 (d, 1H), 7.37 (m, 2H), 6.99 (d, 1H), 6.29 (d, 1H), 5.83 (dd, 1H), 4.71 (s, 2H), 1.56 (s, 9H).

Step 2

N-(2-carboxyindol-5-yl)-2-(4-(5-chloro-2-(1H-tetrazol-1-yl)phenyl))-2-oxo-pyridin-1(2H)-yl)acetamide (Compound 6)

N-(2-tert-butoxycarboxylindol-5-yl)-2-(4-(5-chloro-2-(1H-tetrazol-1-yl)phenyl))-2-oxo-pyridin-1-yl)acetamide (6B) (0.17 g, 0.25 mmol) was dissolved in dichloromethane (2 ml), trifluoroacetic acid (1 ml) was added thereto, and the reaction was allowed to proceed at room temperature for 5 hours. The reaction solution was concentrated, and the residue was washed with dichloromethane/methanol (v/v=1:1) and dried, to give the title compound as a pink solid (70 mg, yield 58%).

¹H NMR (400 MHz, DMSO) δ 11.68 (s, 1H), 10.21 (s, 1H), 9.70 (s, 1H), 7.97 (s, 1H), 7.82 (m, 3H), 7.59 (d, 1H), 7.36 (m, 2H), 7.03 (d, 1H), 6.29 (d, 1H), 5.83 (dd, 1H), 4.71 (s, 2H).

LCMS m/z=490.2 [M+1].

Example 7

N-(4-methoxycarboxylaminophenyl)-7-(5-chloro-2-(1H-tetrazol-1-yl)phenyl)-5-oxo-1,2,3,5-tetrahydroindolizine-3-carboxamide (Compound 7)

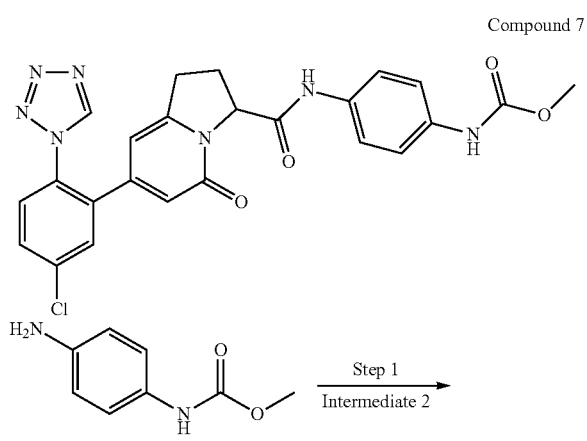

Compound 7

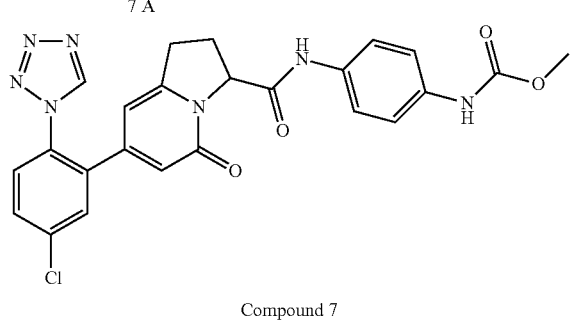

Compound 7

Step 1

N-(4-methoxycarboxylaminophenyl)-7-(5-chloro-2-(1H-tetrazol-1-yl)phenyl)-5-oxo-1,2,3,5-tetrahydroindolizine-3-carboxamide (Compound 7)

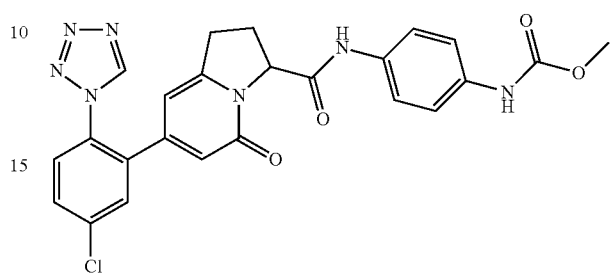

7-(5-chloro-2-(1H-tetrazol-1-yl)phenyl)-5-oxo-1,2,3,5-tetrahydroindolizine-3-carboxylic acid (Intermediate 2) (100 mg, 0.28 mmol) was dissolved in tetrahydrofuran (10 ml), and under a protective nitrogen atmosphere, the solution was cooled to 0° C., oxalyl chloride (0.07 ml, 0.84 mmol) and N,N-dimethylformamide (2 drops) were added dropwise thereto, and the reaction was allowed to proceed for 1.5 hours at room temperature. Tetrahydrofuran was removed under reduced pressure to obtain reaction liquid 1; p-methoxycarbonylaminoaniline (56.5 mg, 0.34 mmol) was dissolved in tetrahydrofuran (5 ml), triethylamine (85 mg, 0.84 mmol) and reaction liquid 1 prepared above were added thereto, and the reaction was allowed to proceed for 2 hours at room temperature. Water (30 ml) was added to the reaction solution, which was extracted with ethyl acetate (50 ml×2). The organic phases were combined, washed with saturated brine (50 mL), dried over anhydrous sodium sulfate, and concentrated. The residue was purified by silica gel column chromatography (dichloromethane:methanol=100:1 to 100:3) to give the title compound N-(4-methoxycarboxylaminophenyl)-7-(5-chloro-2-(1H-tetrazol-1-yl)phenyl)-5-oxo-1,2,3,5-tetrahydroindolizine-3-carboxamide (Compound 7) as an off-white solid (90 mg, yield 64%).

¹H NMR (400 MHz, DMSO) δ 10.32 (s, 1H), 9.69 (s, 1H), 9.55 (s, 1H), 7.80 (m, 3H), 7.49 (d, 2H), 7.38 (d, 2H), 5.97 (s, 1H), 5.93 (s, 1H), 5.06 (dd, 1H), 3.65 (s, 3H), 3.04 (m, 1H), 3.01-2.91 (m, 1H), 2.48-2.39 (m, 1H), 2.19-2.10 (m, 1H).

LCMS m/z=506.3 [M+I].

Example 8

N-(2-carboxyindol-5-yl)-7-(5-chloro-2-(1H-tetrazol-1-yl)phenyl)-5-oxo-1,2,3,5-tetrahydroindolizine-3-carboxamide (Compound 3) (45 mg) was further separated by HPLC using Glison GX-281 (No. CH-Y-C0630) under the following chiral separation condition: Chromatography column: CHIRALPAK IC, 20×250 mm, 5 μm; Mobile phase: A: n-hexane (0.1% TFA), and B: tetrahydrofuran; Process: isocratic elution with A:B=40:60 (v/v) for 20 min; Flow rate: 9 ml/min; Detection wavelength: UV 251 nm; Syringe numbers: 2 syringes (about 20 mg/syringe). Two optical isomers Compound 8-1 (Peak 1, 5 mg, 95.74% pure) and Compound 8-2 (Peak 2, 16 mg, 99.59% pure) were obtained.

Example 9
5-[[2-[4-[5-chloro-2-(tetrazol-1-yl)phenyl]-2-oxo-1-pyridyl]-3-phenyl-propanoyl]amino]-1H-indole-2-carboxylic Acid (Compound 9)
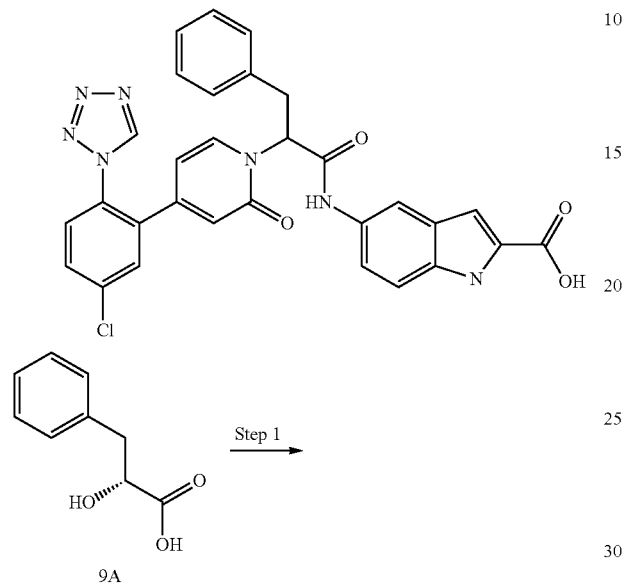
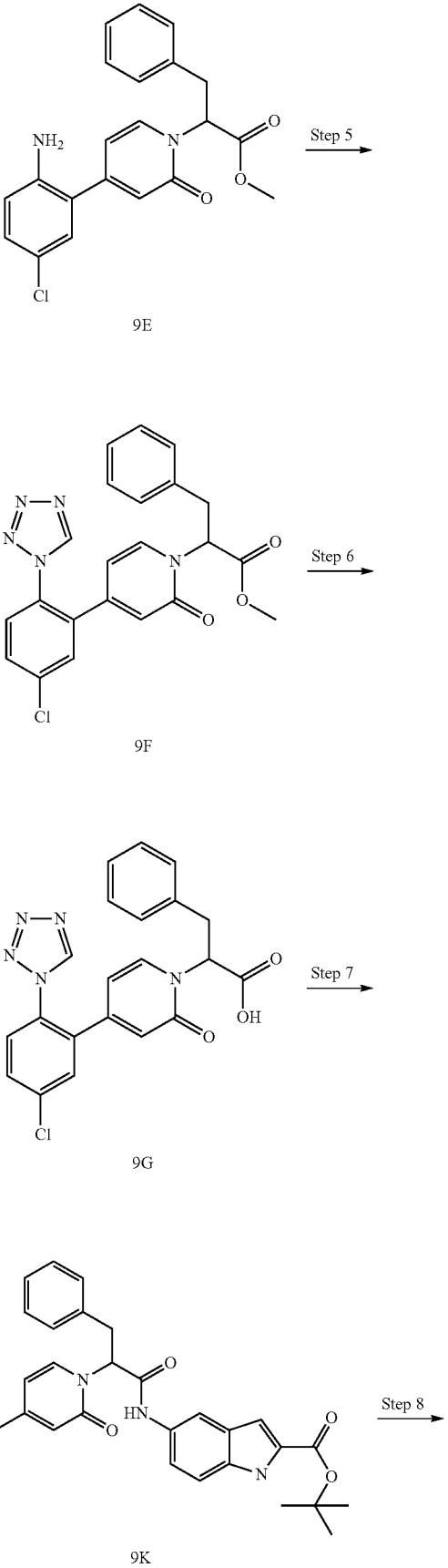

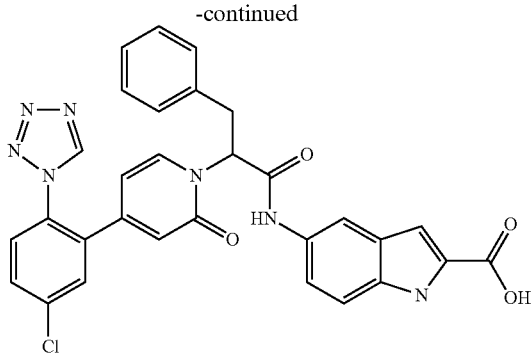

Compound 9

Step 1: Methyl 2-hydroxy-3-phenylpropanonate (9B)

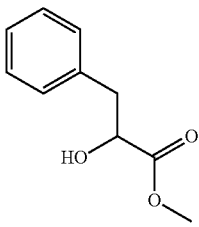

2-hydroxy-3-phenylpropanoic acid (9A) (5 g, 30.1 mmol) was dissolved in methanol (100 mL), concentrated sulfuric acid (1 mL) was added thereto, and the reaction was allowed to proceed at 30° C. overnight. The reaction solution was concentrated, then dissolved with ethyl acetate (50 ml), washed once with saturated sodium bicarbonate (50 ml) and then once with saturated sodium chloride (50 ml), dried over anhydrous sodium sulfate, and concentrated to give methyl 2-hydroxy-3-phenylpropanonate (9B) as a white solid (6 g, 100%).

$^1$H NMR (400 MHz, DMSO) δ 7.30-7.23 (m, 2H), 7.23-7.15 (m, 3H), 5.53 (d, 1H), 4.27-4.22 (m, 1H), 3.60 (s, 3H), 2.95 (dd, 1H), 2.82 (dd, 1H).

Step 2: methyl 2-((trifluoromethylsulfonyl)oxy)-3-phenylpropanoate (9C)

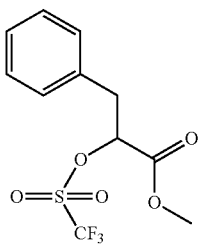

Methyl 2-hydroxy-3-phenylpropanonate (9B) (1 g, 5.5 mmol) was dissolved in chloroform (20 mL); under the protection of nitrogen, triethylamine (0.67 g, 6.6 mmol) and trifluoromethanesufonyl anhydride (1.7 g, 6.1 mmol) were added at −78° C.; the temperature was allowed to sponta- neously rise to room temperature and the reaction was allowed to proceed for 2 hours. Saturated sodium bicarbonate (10 mL) was added to the reaction solution to partition the mixed solution; the organic phase was washed once with saturated sodium chloride (10 mL), dried over anhydrous sodium sulfate, and concentrated; the residue was purified by silica gel column chromatography (petroleum ether:ethyl acetate (v/v)=100:1 to 10:1) to give methyl 2-((trifluoromethylsulfonyl)oxy)-3-phenylpropanoate (9C) as a colorless liquid (1.0 g, yield 62.5%).

$^1$H NMR (400 MHz, DMSO) δ 7.38-7.21 (m, 5H), 5.53 (dd, 1H), 3.77 (s, 3H), 3.30 (dd, 1H), 3.14 (dd, 1H).

Step 3: methyl 2-(4-bromo-2-oxopyridin-1(2H)-yl)-3-phenylpropanoate (9D)

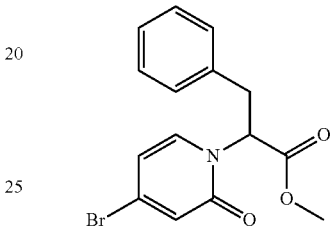

4-bromopyridin-2(1H)-one (77.8 mg, 0.45 mmol) was dissolved in tetrahydrofuran (10 mL), sodium hydride (2 mg, 0.55 mmol) was added at room temperature, and the reaction was allowed to proceed for 10 min. Methyl 2-((trifluoromethylsulfonyl)oxy)-3-phenylpropanoate (9C) (0.15 g, 0.5 mmol) was added thereto and the reaction was allowed to proceed at 30° C. overnight. The reaction solution was added to water (10 ml), and extracted with ethyl acetate (10 ml×3). The organic phases were combined, washed with water (50 ml×2), dried over anhydrous sodium sulfate, and concentrated. The residue was purified by silica gel column chromatography (petroleum ether:ethyl acetate (v/v)=10:1 to 2:1) to give methyl 2-(4-bromo-2-oxopyridin-1(2H)-yl)-3-phenylpropanoate (9D) as a white solid (50 mg, yield 33.0%).

$^1$H NMR (400 MHz, DMSO) δ 7.34 (d, 1H), 7.28-7.13 (m, 3H), 7.09 (d, 2H), 6.68 (d, 1H), 6.31 (dd, 1H), 5.37 (dd, 1H), 3.67 (s, 3H), 3.39 (ddd, 2H).

LCMS m/z=336.1[M−1].

Step 4: methyl 2-(4-(2-amino-5-chlorophenyl)-2-oxopyridin-1(2H)-yl)-3-phenylpropanoate (9E)

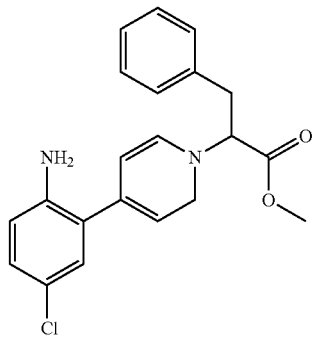 [SMILES: COC(=O)C(Cc1ccccc1)N1C=CC(c2cc(Cl)ccc2N)=CC1]

Methyl 2-(4-bromo-2-oxopyridin-1(2H)-yl)-3-phenylpropanoate (9D) (5.7 g, 17.0 mmol) was dissolved in dioxane (100 mL), then 4-chloro-2-(4,4,5,5-tetramethyl-1,3,2-dioxaborolan-2-yl)aniline (8.6 g, 34.0 mmol) and [1,1'-bis(diphenylphosphino)ferrocene]dichloropalladium (Pd(dppf)Cl₂) (0.31 g, 0.42 mmol) and an aqueous solution of saturated sodium bicarbonate (30 mL) were added thereto, and the reaction was allowed to proceed at 110° C. overnight under N₂ protection. The reaction solution was added to 100 ml water, and extracted with ethyl acetate (100 ml×3). The organic phases were combined, washed with water (50 ml×2), dried over anhydrous sodium sulfate, and concentrated. The residue was purified by silica gel column chromatography (petroleum ether:ethyl acetate (v/v)=10:1 to 5:1) to give methyl 2-(4-(2-amino-5-chlorophenyl)-2-oxopyridin-(2H)-yl)-3-phenylpropanoate (9E) as a yellow solid (1.4 g, yield 21.5%).

LCMS m/z=383.2[M−1].

Step 5: methyl 2-(4-(5-chloro-2-(1H-tetrazol-1-yl)phenyl)-2-oxopyridin-1(2H)-yl)-3-phenylpropanoate (9F)

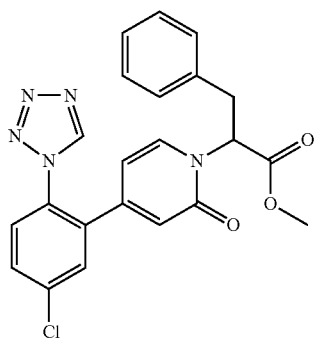 [SMILES: COC(=O)C(Cc1ccccc1)n1ccc(-c2cc(Cl)ccc2-n2cnnn2)cc1=O]

Methyl 2-(4-(2-amino-5-chlorophenyl)-2-oxopyridin-1(2H)-yl)-3-phenylpropanoate (9E) (0.7 g, 2.0 mmol) was dissolved in 20 ml anhydrous acetic acid, and trimethyl orthoformate (1.3 g, 12.5 mmol) was added thereto, followed by stirring at room temperature for 5 min. Sodium azide (0.8 g, 12.5 mmol) was added, and the reaction was allowed to proceed at 80° C. overnight. The reaction solution was added to water (50 mL) and extracted with ethyl acetate (10 mL×3). The organic phases were combined, washed with water (10 ml×2), dried over anhydrous sodium sulfate, and concentrated to give methyl 2-(4-(5-chloro-2-(1H-tetrazol-1-yl)phenyl)-2-oxopyridin-1(2H)-yl)-3-phenylpropanoate (9F) as a yellow solid (0.7 g, yield 77.7%).

¹H NMR (400 MHz, DMSO) δ 9.59 (s, 1H), 8.00-7.55 (m, 3H), 7.26 (t, 2H), 7.21-7.19 (m, 2H), 6.96 (d, 2H), 6.24 (d, 1H), 5.66 (dd, 1H), 5.20 (dd, 1H), 3.65 (s, 3H), 3.35 (d, 1H), 3.33-3.27 (m, 1H).

LCMS m/z=458.3[M+23].

Step 6

2-(4-(5-chloro-2-(1H-tetrazol-1-yl)phenyl)-2-oxopyridin-1(2H)-yl)-3-phenylpropanoic Acid (9G)

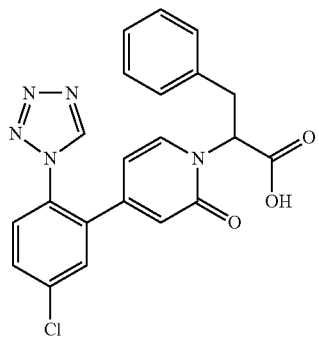 [SMILES: O=C(O)C(Cc1ccccc1)n1ccc(-c2cc(Cl)ccc2-n2cnnn2)cc1=O]

Methyl 2-(4-(5-chloro-2-(H-tetrazol-1-yl)phenyl)-2-oxopyridin-1(2H)-yl)-3-phenylpropanoate (9F) (0.7 g, 1.6 mmol) was dissolved in 10 ml tetrahydrofuran, and a 2 ml aqueous solution of lithium hydroxide (0.2 g, 4.8 mmol) was added thereto, followed by reaction at room temperature for 5 hours. The reaction solution was added to water (20 mL), adjusted to a pH of about 2 with a 6 mol/L hydrochloric acid solution, and extracted with ethyl acetate (50 mL×3). The organic phases were combined, wash with water (50 ml×2), dried over anhydrous sodium sulfate, and concentrated to give 2-(4-(5-chloro-2-(1H-tetrazol-1-yl)phenyl)-2-oxopyridin-1(2H)-yl)-3-phenylpropanoic acid (9G) as a red solid (0.6 g, yield 89.6%).

LCMS m/z=522.2[M+1].

Step 7: tert-butyl 5-(2-(4-(5-chloro-2-(1H-tetrazol-1-yl)phenyl)-2-oxopyridin-1(2H)-yl)-3-phenylpropanamido)-1H-indole-2-carboxylate (9K)

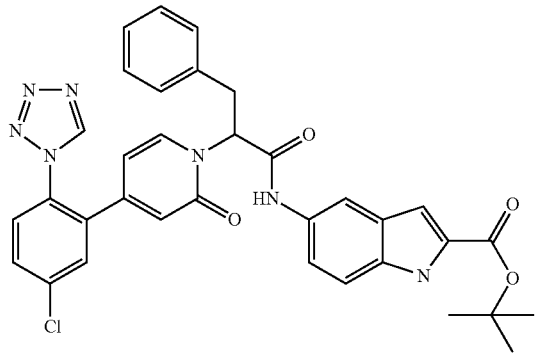 [SMILES: CC(C)(C)OC(=O)c1cc2cc(NC(=O)C(Cc3ccccc3)n3ccc(-c4cc(Cl)ccc4-n4cnnn4)cc3=O)ccc2[nH]1]

2-(4-(5-chloro-2-(1H-tetrazol-1-yl)phenyl)-2-oxopyridin-1(2H)-yl)-3-phenylpropanoic acid (9G) (0.7 g, 1.67 mmol), t-butyl 5-amino-H-indole-2-carboxylate (0.38 g, 1.67 mmol) and 1-(3-dimethylaminopropyl)-3-ethyl-carbodiimide hydrochloride (1.27 g, 6.6 mmol) were added to 10 ml pyridine, and allowed to react at room temperature for 4 hours. The reaction solution was added to a 1 mol/LHCl solution to pH=2, water (50 ml) was added thereto, and the solution was extracted with ethyl acetate (50 ml×3). The organic phases were combined, washed with water (50 ml×2), dried over anhydrous sodium sulfate, and concentrated. The residue was purified by silica gel column chromatography (dichloromethane:methanol (v/v)=100:1 to 50:1) to give tert-butyl 5-(2-(4-(5-chloro-2-(H-tetrazol-1-yl)phenyl)-2-oxopyridin-(2H)-yl)-3-phenylpropanamido)-1H-indole-2-carboxylate (9K) as a yellow solid (0.7 g, yield 66.7%).

Step 8

5-[[2-[4-[5-chloro-2-(tetrazol-1-yl)phenyl]-2-oxo-1-pyridyl]-3-phenyl-propanoyl]amino]-1H-indole-2-carboxylic Acid (Compound 9)

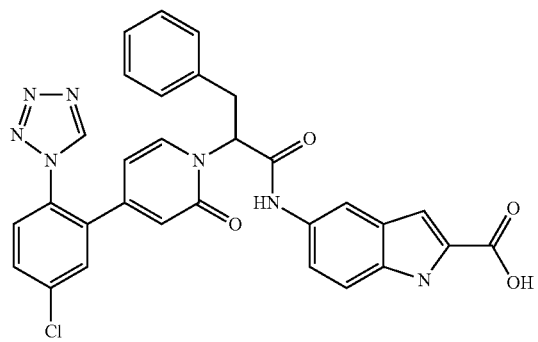 [SMILES: O=C(O)c1cc2cc(NC(=O)C(Cc3ccccc3)n3ccc(-c4cc(Cl)ccc4-n4cnnn4)cc3=O)ccc2[nH]1]

Tert-butyl 5-(2-(4-(5-chloro-2-(1H-tetrazol-1-yl)phenyl)-2-oxopyridin-1(2H)-yl)-3-phenylpropanamido)-1H-indole-2-carboxylate (9K) (0.5 g, 0.78 mmol) was dissolved in dichloromethane (10 ml) and trifluoroacetic acid (5 ml), and the reaction was allowed to proceed at room temperature for 8 hours. The reaction solution was concentrated, and the residue was purified by silica gel column chromatography (dichloromethane:methanol (v/v)=100:1 to 20:1) to give 5-[[2-[4-[5-chloro-2-(tetrazol-1-yl)phenyl]-2-oxo-1-pyridyl]-3-phenyl-propanoyl]amino]-1H-indole-2-carboxylic acid (Compound 9) as a yellow solid (20 mg, yield 4.4%).

$^1$H NMR (400 MHz, DMSO) δ 11.71 (s, 1H), 10.42 (s, 1H), 9.60 (s, 1H), 7.99 (s, 1H), 7.90 (d, 1H), 7.79-7.76 (m, 3H), 7.39-7.26 (m, 4H), 7.21-7.15 (m, 3H), 7.05 (s, 1H), 6.20 (s, 1H), 5.95-5.94 (m, 1H), 5.81 (d, 2H), 3.37-3.23 (m, 2H).

LCMS m/z=578.2[M−1].

Example 10

5-(7-(5-chloro-2-(1H-tetrazol-1-yl)phenyl)-5-oxo-1,2,3,5-tetrahydroindolizine-3-carboxamido)-1-methyl-1H-indole-2-carboxylic Acid (Compound 10)

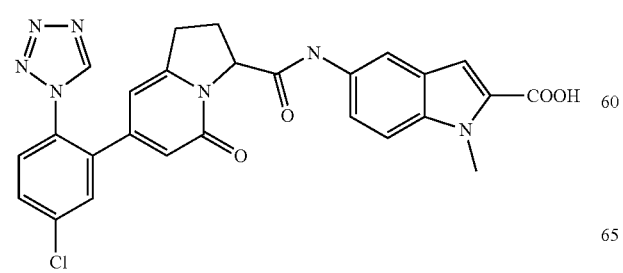

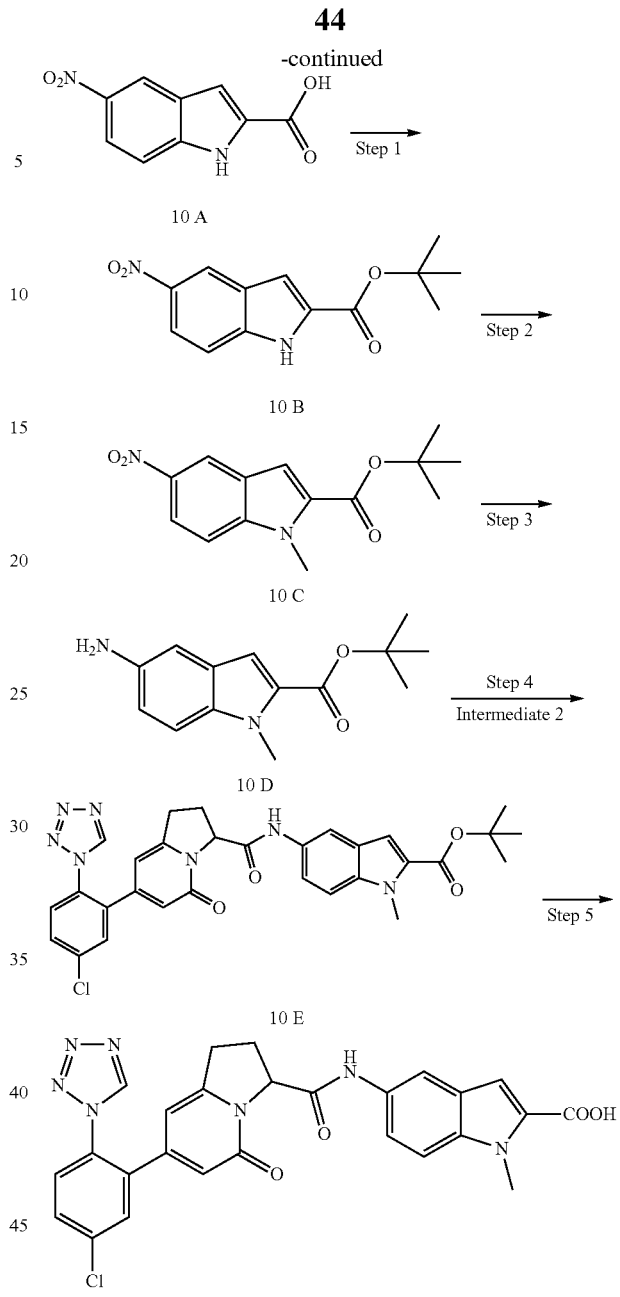

Step 1: t-butyl 5-nitro-1H-indole-2-carboxylate (10B)

The starting material 5-nitro-1H-indole-2-carboxylic acid (5.0 g, 24.2 mmol) was dissolved in tetrahydrofuran (100 mL), oxalyl chloride (5.5 mL, 60.5 mmol) was added, and 2 drops of N,N-dimethylformamide were added dropwise, followed by reaction at room temperature for 2 hours. The solvent and excess oxalyl chloride were removed under reduced pressure, the residue was dissolved by addition of tetrahydrofuran (100 mL), and potassium t-butoxide (8.1 g, 72.6 mmol) was added, followed by reaction at room temperature overnight. The reaction solution was directly concentrated under reduced pressure, and passed through a silica gel column to obtain t-butyl 5-nitro-1H-indole-2-carboxylate (10B) as a yellow solid (4.0 g, yield 62.5%).

$^1$H NMR (400 MHz, DMSO) δ 12.39 (s, 1H), 8.71 (d, 1H), 8.12 (dd, 1H), 7.61 (d, 1H), 7.34 (d, 1H), 1.59 (s, 9H).

Step 2: tert-butyl 1-methyl-5-nitro-1H-indole-2-carboxylate (10C)

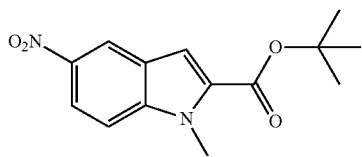

t-butyl 5-nitro-1H-indole-2-carboxylate (10B) (0.5 g, 1.9 mmol) was dissolved in N,N-dimethylformamide (5 mL), and potassium carbonate (0.525 g, 3.8 mmol) and iodomethane (0.295 g, 2.1 mmol) were added thereto, followed by reaction at room temperature for 2 hours. Ethyl acetate (60 mL) was added, followed by washing with water (60 ml×2) and saturated brine (60 mL), drying over anhydrous sodium sulfate, and concentration under reduced pressure, to obtain tert-butyl 1-methyl-5-nitro-1H-indole-2-carboxylate (10C) as a yellow solid (0.5 g, yield 95.2%).

$^1$H NMR (400 MHz, DMSO) δ 8.70 (d, 1H), 8.15 (dd, 1H), 7.78 (d, 1H), 7.44 (d, 1H), 4.06 (s, 3H), 1.59 (s, 9H). LCMS m/z=277.1 [M+1].

Step 3: tert-butyl 5-amino-1-methyl-1H-indole-2-carboxylate (10D)

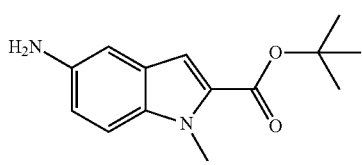 [SMILES: Cn1c(C(=O)OC(C)(C)C)cc2cc([N+](=O)[O-])ccc21]

tert-butyl 1-methyl-5-nitro-1H-indole-2-carboxylate (10C) (1.5 g, 5.4 mmol) was dissolved in methanol (30 mL), Pd/C (0.45 g) was added thereto, and hydrogen gas was introduced, followed by reaction at room temperature for 2 hours. The Pd/C was filtered off, and the filtrate was concentrated under reduced pressure to obtain tert-butyl 5-amino-1-methyl-1H-indole-2-carboxylate (10D) as a yellow solid (0.9 g, yield 69.2%).

$^1$H NMR (400 MHz, CDCl$_3$) δ 7.18 (d, 1H), 7.02 (s, 1H), 6.93 (d, 1H), 6.83 (dd, 1H), 3.99 (s, 3H), 1.60 (s, 9H). LCMS m/z=247.1 [M+1].

Step 4: tert-butyl 5-(7-(5-chloro-2-(1H-tetrazol-1-yl) phenyl)-5-oxo-1,2,3,5-tetrahydroindolizine-3-carboxamido)-1-methyl-1H-indole-2-carboxylate (10E)

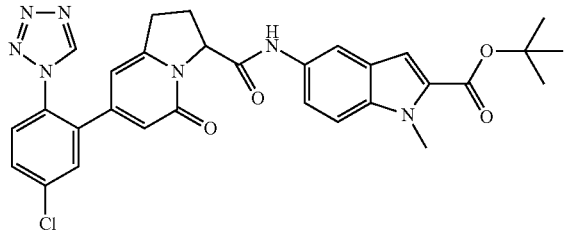 [SMILES: Cn1c(C(=O)OC(C)(C)C)cc2cc(NC(=O)C3CCc4cc(-c5cc(Cl)ccc5-n5cnnn5)cc(=O)n43)ccc21]

7-(5-chloro-2-(1H-tetrazol-1-yl)phenyl)-5-oxo-1,2,3,5-tetrahydroindolizine-3-carboxylic acid (Intermediate 2) (1.3 g, 3.6 mmol) was dissolved in tetrahydrofuran (20 mL), and under N$_2$ protection, oxalyl chloride (1 mL, 10.8 mmol) and 2 drops of N,N-dimethylformamide were added dropwise thereto, and the reaction was allowed to proceed for 1 hour at room temperature. The solvent was removed under reduced pressure, and the resultant solution was ready for use. Tert-butyl 5-amino-1-methyl-1H-indole-2-carboxylate (10D) (0.9 g, 3.6 mmol) was dissolved in tetrahydrofuran (20 ml), triethylamine (1.5 mL, 10.8 mmol) was added thereto, and the above solution ready for use (20 ml) was added dropwise, followed by reaction at room temperature for 2 hours. Ethyl acetate (100 ml) was added to the reaction solution, which was washed sequentially with water (100 ml) and saturated brine (100 ml), dried over anhydrous sodium sulfate, concentrated under reduced pressure, and passed through a silica gel column, to obtain tert-butyl 5-(7-(5-chloro-2-(1H-tetrazol-1-yl)phenyl)-5-oxo-1,2,3,5-tetrahydroindolizine-3-carboxamido)-1-methyl-1H-indole-2-carboxylate (10E) as a light tan solid (1.3 g, yield 61.9%).

$^1$H NMR (400 MHz, CDCl$_3$) δ 10.06 (s, 1H), 8.58 (s, 1H), 7.93 (d, 1H), 7.61 (dd, 1H), 7.57-7.51 (m, 2H), 7.24 (dd, 1H), 7.10 (d, 1H), 7.02 (s, 1H), 6.36 (s, 1H), 5.74 (s, 1H), 5.44 (d, 1H), 3.94 (s, 3H), 3.44-3.22 (m, 1H), 2.87 (ddd, 2H), 2.39-2.24 (m, 1H), 1.60 (s, 9H).
LCMS m/z=586.2 [M+1].

Step 5

5-(7-(5-chloro-2-(1H-tetrazol-1-yl)phenyl)-5-oxo-1,2,3,5-tetrahydroindolizine-3-carboxamido)-1-methyl-1H-indole-2-carboxylic Acid (Compound 10)

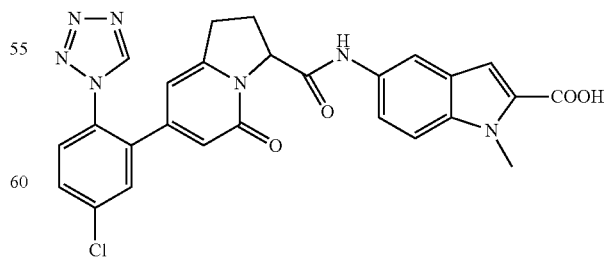

Tert-butyl 5-(7-(5-chloro-2-(1H-tetrazol-1-yl)phenyl)-5-oxo-1,2,3,5-tetrahydroindolizine-3-carboxamido)-1-methyl-1H-indole-2-carboxylate (10E) (1.3 g, 2.2 mmol)

was dissolved in dichloromethane (10 mL), and trifluoroacetic acid (2.5 g, 22 mmol) was added, followed by reaction at room temperature for 4 hours. Dichloromethane and trifluoroacetic acid were removed under reduced pressure, and the residue was dissolved by addition of dichloromethane (100 mL). The solution was adjusted to a pH of about 7 with an aqueous solution of saturated sodium bicarbonate, washed sequentially with water (60 mL) and saturated brine (60 mL), dried over anhydrous sodium sulfate, concentrated under reduced pressure, and passed through a silica gel column, to obtain 5-(7-(5-chloro-2-(1H-tetrazol-1-yl)phenyl)-5-oxo-1,2,3,5-tetrahydroindolizine-3-carboxamido)-1-methyl-1H-indole-2-carboxylic acid (Compound 10) as a yellow solid (0.56 g, yield 51%).

$^1$H NMR (400 MHz, DMSO) δ 10.44 (s, 1H), 9.71 (s, 1H), 8.04 (d, 1H), 7.81 (dd, 3H), 7.53 (d, 1H), 7.44 (dd, 1H), 7.16 (s, 1H), 5.99 (s, 1H), 5.94 (s, 1H), 5.14 (dd, 1H), 4.00 (s, 3H), 3.09 (dt, 1H), 3.04-2.93 (m, 1H), 2.49-2.41 (m, 1H), 2.26-2.14 (m, 1H).

LCMS m/z=530.1 [M+1].

Test Examples

Test Example 1. In Vitro Inhibitory Effect of the Compounds of the Present Invention on the Enzymatic Activity of Blood-Coagulation Factor XIa The following method was used to test the in vitro inhibitory effect of the compounds of the present invention on the activity of human blood-coagulation factor XIa, expressed by the Inhibition constant Ki.

Solution preparation: reaction buffer: 0.03M HEPES acid, 0.145M NaCl, 0.005 M KCl, 0.1% PEG-8000, pH=7.5;

HEPES 8.499 g, NaCl 8.47 g, KCl 0.3725, PEG 8000 1 g, plus ddH$_2$O 800 ml; the pH was adjusted to 7.4 with HCl, and the volume was metered to 1 L.

S2366 substrate stock solution (2 mM): a volume of substrate (25 ml) was dissolved in 23 ml sterile deionized water, aliquoted, and stored at 4° C. in darkness.

S2366 substrate working solution: the stock solution was diluted by 4 folds with the reaction buffer before use.

FXIa working solution: 1 μl FXIa stock solution was added to 10 ml reaction buffer and thoroughly mixed before use.

Method: 15 μl test sample working solution (15 μl DMSO for the control group) and 75 μl FXIa working solution were added to a 96-well plate, and incubated at room temperature for 15 min. Then 60 μl S2366 substrate working solution was added to initiate the reaction. The absorbance at 405 nm for the test compounds was continually assayed once every 3 minutes, and a ΔA-time curve was plotted to calculate the slope as the reaction rate. In accordance with the following equation, IC50 of each test sample when the substrate concentration was 200 μM was calculated with spss 16.0. Inhibition (I %) and Ki of the test samples were calculated in accordance with the follow equations, and the results are shown in Table 1.

$$I\% = (V0 - Vi)/V0 \times 100$$

where V0 is the reaction rate in the control wells, and Vi is the reaction rate in the test sample wells;

$$IC50 = Ki(1 + [S]/Km)$$

where Km=0.2 mM, and [S] is the substrate concentration=200 μM.

TABLE 1

Experimental results of in vitroassays of enzymatic activity of blood-coagulation factor XIa

| Compound No. | Ki (μM) |
|---|---|
| 1 | 0.249 |
| 2 | 0.068 |
| 3 | 0.009 |
| 4 | 0.017 |
| 5 | 0.146 |
| 6 | 0.014 |
| 7 | 0.344 |
| 8-1 | 0.002 |
| 8-2 | 1.030 |
| 9 | 0.004 |

Conclusion: the compounds of the present invention have a significant in vitroinhibitory effect on the activity of human blood-coagulation factor XIa.

Conclusion: the compounds of the present invention have a significant in vitro inhibitory effect on the activity of human blood-coagulation factor XIa.

Test Example 2. In Vitro Assay of the Blood Coagulation Function of Human Plasma 20 ml blood was taken by venipuncture from the ulnar vein of each of 20 healthy volunteers aged 25 to 35 years who had not taken any medicines within last one week, and was collected in a sodium citrate anticoagulation tube, with the ratio of anticoagulant to blood being 1:9 (v/v). Anticoagulation blood was taken and centrifuged at 200 g for 15 min, the supernatant therefrom was taken and centrifuged at 2000 g for 15 min, and then the supernatant therefrom was collected, well mixed, separated into 4 to 5 ml aliquots, and stored at −80° C. For APTT and PT assays, a plasma sample was taken and rapidly thawed in a 37° C. water bath, and 6 μl test compound working solution was added per 294 μl plasma, while 6 μl DMSO was added for the blank control. The compounds and plasma were well mixed, and assayed in a coagulometer. The concentration of the compounds (EC$_{2x}$) required to double the plasma APTT was determined with origin 8.5, and the results are shown in Table 2.

TABLE 2

Anti-coagulation effect of the compounds of the present invention on human plasma (represented by PT EC$_{2x}$ and aPTT EC$_{2x}$)

| Example No. | aPTT EC$_{2x}$(μM) |
|---|---|
| 3 | 6.1 |
| 4 | 9.5 |
| 6 | 9.0 |
| 8-1 | 2.3 |
| 9 | 6.4 |

Conclusion: the compounds of the present invention have a significant in vitroanti-coagulation effect on human plasma.

Conclusion: the compounds of the present invention have a significant in vitro anti-coagulation effect on human plasma.

The invention claimed is:
1. A compound represented by general formula (II):

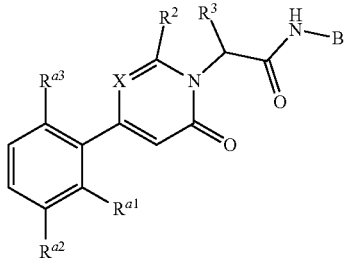

wherein
$R^{a1}$ or $R^{a2}$ is each independently selected from H, F, Cl, Br, I, cyano, formyl, acetyl, a $C_{1-4}$ alkyl, a $C_{1-4}$ alkoxy, —C(=O)$C_{1-4}$ alkyl or a 5-membered heterocycle, wherein the heterocycle contains 1 to 4 heteroatoms selected from N, O or S, and the alkyl, alkoxy or heterocycle is optionally further substituted with 0 to 5 substituents selected from H, F, Cl, Br or I;
$R^{a3}$ is formyl, acetyl, —C(=O)$C_{1-4}$ alkyl or a 5-membered heterocycle, wherein the heterocycle contains 1 to 4 heteroatoms selected from N, O or S, and the alkyl, alkoxy or heterocycle is optionally further substituted with 0 to 5 substituents selected from H, F, Cl, Br or I;
X is selected from N or CH;
when X is CH, B is selected from one of the following structures, which is substituted or unsubstituted:

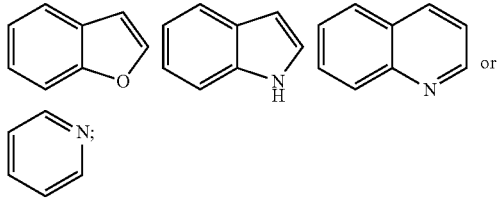

and, if substituted it is optionally substituted with 1 to 5 $R^b$s,
when X is N, B is selected from one of the following structures, which is substituted or unsubstituted:

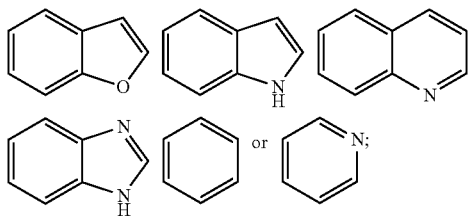

and if substituted, it is optionally substituted with 1 to 5 $R^b$s;
the $R^b$s are each independently selected from H, F, Cl, Br, I, hydroxyl, amino, carboxy, —NHC(=O)$R^{b2}$, —C(=O)N$R^{b1}R^{b2}$ or —C(=O)$R^{b1}$;
$R^{b1}$ and $R^{b2}$ are each independently selected from H, hydroxy, amino, a $C_{1-4}$ alkyl or a $C_{1-4}$ alkoxy, wherein the alkyl or alkoxy is optionally further substituted with 0 to 4 substituents selected from H, F, Cl, Br, I or hydroxyl;

$R^2$ is selected from H, F, Cl, Br, I or a $C_{1-4}$ alkyl;
$R^3$ is selected from H, a $C_{1-4}$ alkyl or —(CH$_2$)$_n$-(5- or 6-membered carbocycle), wherein the carbocycle is optionally further substituted with 0 to 5 substituents selected from H, F, Cl, Br, I, hydroxy, amino, carboxy, a $C_{1-4}$ alkyl or a $C_{1-4}$ alkoxy; and
n is selected from 0, 1, 2, 3, or 4,
or a stereoisomer, an oxynitride, a metabolite, a pharmaceutically acceptable salt or co-crystal thereof.
2. The compound according to claim 1, wherein the compound is selected from the compounds represented by general formula (III):

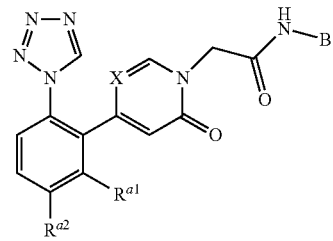

wherein
$R^{a1}$ or $R^{a2}$ is each independently selected from H, F, Cl, Br, I, cyano, formyl, acetyl, a $C_{1-4}$ alkyl, or a $C_{1-4}$ alkoxy, wherein the alkyl or alkoxy is optionally further substituted with 0 to 5 substituents selected from H, F, Cl, Br or I;
when X is CH, B is

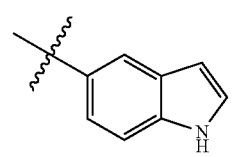 [SMILES: *c1ccc2[nH]ccc2c1]

which is substituted or unsubstituted; and if substituted, it is optionally substituted with 1 to 5 $R^b$s,
when X is N, B is

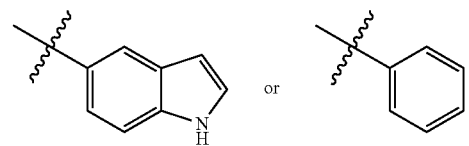 [SMILES: *c1ccc2[nH]ccc2c1 ; *c1ccccc1]

which is substituted or unsubstituted; and if substituted, it is optionally substituted with 1 to 5 $R^b$s,
the $R^b$s are each independently selected from H, F, Cl, Br, I, hydroxyl, amino, carboxy, —NHC(=O)$R^{b2}$, —C(=O)N$R^{b1}R^{b2}$ or —C(=O)$R^{b1}$; and
$R^{b1}$ and $R^{b2}$ are each independently selected from H, hydroxy, amino, trifluoromethyl, methyl, ethyl, isopropyl, methoxy or ethoxy,
or a stereoisomer, an oxynitride, a metabolite, a pharmaceutically acceptable salt or co-crystal thereof.
3. The compound according to claim 2, wherein:
$R^{a1}$ or $R^{a2}$ is each independently selected from H, F, Cl, or Br; and $R^b$s are each independently selected from H, carboxy, —C(=O)NH$_2$ or —NHC(=O)OCH$_3$, or a stereoisomer, an oxynitride, a metabolite, a pharmaceutically acceptable salt or co-crystal thereof.

4. A compound represented by general formula (II):

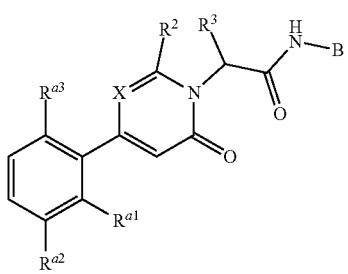

(II)

wherein $R^{a1}$, $R^{a2}$ or $R^{a3}$ is each independently selected from the group consisting of H, F, Cl, Br, I, cyano, formyl, acetyl, a C$_{1-4}$ alkyl, a C$_{1-4}$ alkoxy, —C(=O)C$_{1-4}$ alkyl and a 5-membered heterocycle, wherein the heterocycle contains 1 to 4 heteroatoms selected from the group consisting of N, O and S, and the alkyl, alkoxy or heterocycle is optionally further substituted with 0 to 5 substituents selected from the group consisting of H, F, Cl, Br and I;

B is selected from one of the following structures, which is substituted or unsubstituted:

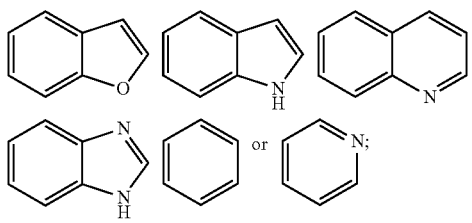

and if substituted, it is optionally substituted with 1 to 5 $R^b$s, the $R^b$s are each independently selected from the group consisting of H, F, Cl, Br, I, hydroxyl, amino, carboxy, —NHC(=O)R$^{b2}$, —C(=O)NR$^{b1}$R$^{b2}$ and —C(=O)R$^{b1}$;

$R^{b1}$ and $R^{b2}$ are each independently selected from the group consisting of H, hydroxy, amino, a C$_{1-4}$ alkyl and a C$_{1-4}$ alkoxy, wherein the alkyl or alkoxy is optionally further substituted with 0 to 4 substituents selected from the group consisting of H, F, Cl, Br, I and hydroxyl;

$R^2$ and $R^3$ form, together with the atoms attached thereto, a 5- to 6-membered heterocycle, containing 1 to 4 heteroatoms selected from the group consisting of N, O and S, wherein the heterocycle is optionally further substituted with 0 to 3 substituents selected from the group consisting of H, F, Cl, Br, I, hydroxy, a C$_{1-4}$ alkyl and a C$_{1-4}$ alkoxy;

X is N or CH; and n is selected from 0, 2, 3, or 4, or a stereoisomer, an oxynitride, a metabolite, a pharmaceutically acceptable salt or co-crystal thereof.

5. A method for treating diseases associated with blood-coagulation factor XIa in a subject, comprising administering the compound according to claim 1, or a stereoisomer, an oxynitride, a metabolite, a pharmaceutically acceptable salt or co-crystal thereof to the subject, wherein the diseases associated with blood-coagulation factor XIa are selected from the group consisting of thromboembolic diseases, including venous thrombosis, deep vein thrombosis, thrombophlebitis, cerebral arterial thrombosis, arterial embolism, coronary thrombosis, pulmonary embolism, renal embolism, cerebral embolism, atherosclerosis, acute coronary syndrome, unstable angina, acute coronary arterial syndrome, myocardial infarction, arteriosclerosis, sudden ischemic death, transient ischemia, peripheral arterial occlusive disease, stroke, and cerebrovascular diseases.

6. The compound according to claim 4, wherein the compound is selected from the compounds represented by general formula (IV):

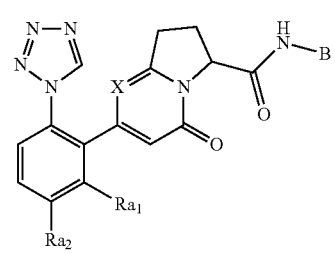

(IV)

wherein $R^{a1}$ or $R^{a2}$ is each independently selected from H, F, Cl, Br, I, cyano, formyl, acetyl, a C$_{1-4}$ alkyl, or a C$_{1-4}$ alkoxy, wherein the alkyl or alkoxy is optionally further substituted with 0 to 5 substituents selected from H, F, Cl, Br or I;

B is selected from one of

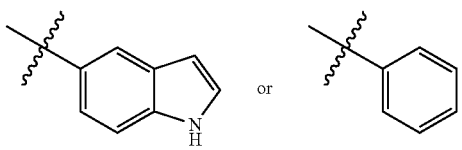 [SMILES: *c1ccc2[nH]ccc2c1 ; *c1ccccc1]

which is substituted or unsubstituted; and if substituted, it is optionally substituted with 1 to 5 $R^b$s, the $R^b$s are each independently selected from H, F, Cl, Br, I, hydroxyl, amino, carboxy, —NHC(=O)R$^{b2}$, —C(=O)NR$^{b1}$R$^{b2}$ or —C(=O)R$^{b1}$; and $R^{b1}$ and $R^{b2}$ are each independently selected from H, hydroxy, amino, trifluoromethyl, methyl, ethyl, isopropyl, methoxy or ethoxy, or a stereoisomer, an oxynitride, a metabolite, a pharmaceutically acceptable salt or co-crystal thereof.

7. A The compound according to claim 3, wherein:

$R^{a1}$ or $R^{a2}$ is each independently selected from H, F, Cl, or Br; and $R^b$s are each independently selected from H, carboxy, —C(=O)NH$_2$ or —NHC(=O)OCH$_3$, or a stereoisomer, an oxynitride, a metabolite, a pharmaceutically acceptable salt or co-crystal thereof.

8. A compound, wherein the compound is selected from:
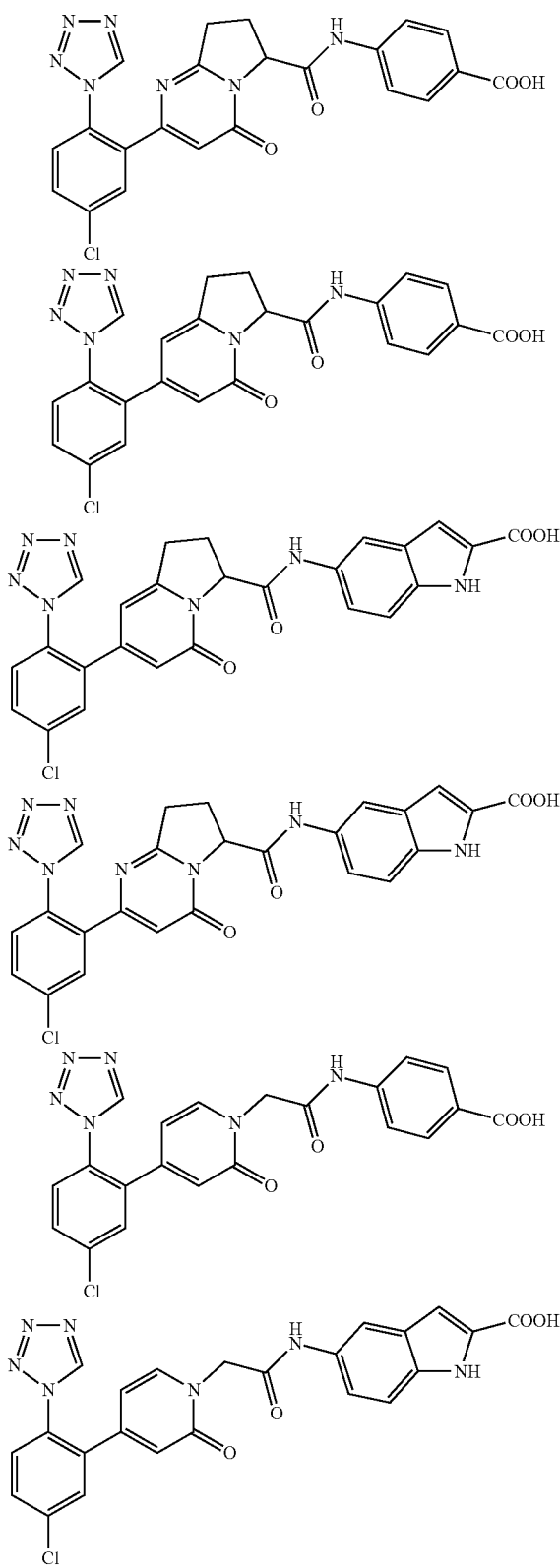
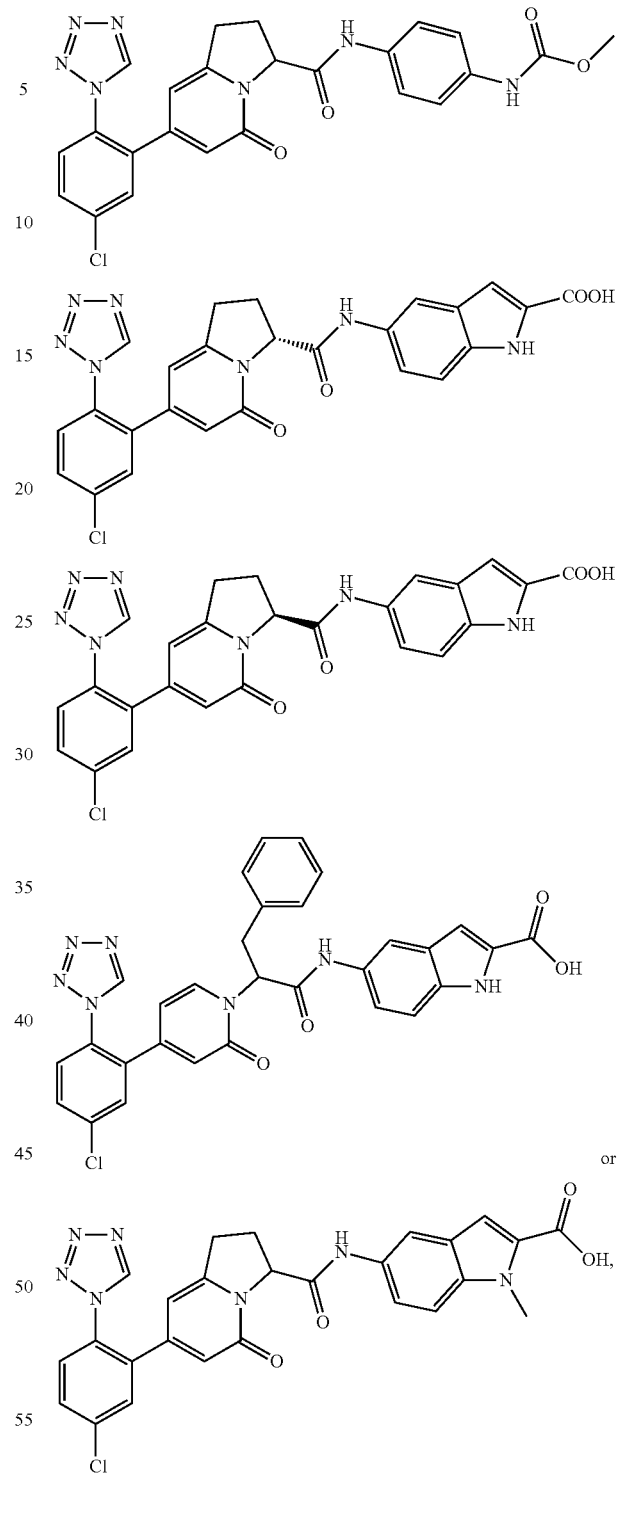
or a stereoisomer, an oxynitride, a metabolite, a pharmaceutically acceptable salt or co-crystal thereof.
* * * * *